US010351870B2

(12) United States Patent
Bauer et al.

(10) Patent No.: US 10,351,870 B2
(45) Date of Patent: Jul. 16, 2019

(54) USES OF NOVEL FATTY ACID DESATURASES AND ELONGASES AND PRODUCTS THEREOF

(71) Applicant: BASF Plant Science Company GmbH, Ludwigshafen (DE)

(72) Inventors: Jörg Bauer, Teltow (DE); Johnathan A. Napier, Preston (GB); Olga Sayanova, Redbourn (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 0 days.

(21) Appl. No.: 15/351,962

(22) Filed: Nov. 15, 2016

(65) Prior Publication Data
US 2017/0067070 A1 Mar. 9, 2017

Related U.S. Application Data

(63) Continuation of application No. 13/384,277, filed as application No. PCT/EP2010/060178 on Jul. 15, 2010, now Pat. No. 9,493,520.

(60) Provisional application No. 61/226,301, filed on Jul. 17, 2009.

(30) Foreign Application Priority Data

Jul. 17, 2009 (EP) ..................................... 09165752

(51) Int. Cl.
C12N 15/82 (2006.01)
A23D 9/00 (2006.01)
C07K 14/435 (2006.01)
C12N 9/02 (2006.01)
C12N 9/00 (2006.01)

(52) U.S. Cl.
CPC ........ *C12N 15/8247* (2013.01); *C07K 14/435* (2013.01); *C12N 9/0071* (2013.01); *C12N 9/93* (2013.01); *C12Y 114/19* (2013.01); *C12Y 114/19003* (2013.01); *C12Y 114/19004* (2013.01); *C12Y 114/19006* (2013.01); *C12Y 602/01003* (2013.01)

(58) Field of Classification Search
None
See application file for complete search history.

(56) References Cited

U.S. PATENT DOCUMENTS

| | | | |
|---|---|---|---|
| 7,045,683 B2 | 5/2006 | Mukerji et al. | |
| 8,247,653 B2 | 8/2012 | Das et al. | |
| 8,785,727 B2 | 7/2014 | Bauer et al. | |
| 8,809,559 B2 | 8/2014 | Petrie et al. | |
| 2010/0227924 A1* | 9/2010 | Cirpus ................. | C12N 9/0083 426/601 |

FOREIGN PATENT DOCUMENTS

| | | | |
|---|---|---|---|
| WO | WO-02/090493 A2 | 11/2002 | |
| WO | WO-2007096387 A1 * | 8/2007 | ........... C12N 9/0083 |
| WO | WO-2008/124048 A2 | 10/2008 | |
| WO | WO-2009/124101 A1 | 10/2009 | |
| WO | WO-2010/042510 A1 | 4/2010 | |
| WO | WO-2010/057246 A1 | 5/2010 | |
| WO | WO-2010/142522 A2 | 12/2010 | |
| WO | WO-2011/064183 A1 | 6/2011 | |

OTHER PUBLICATIONS

Arondel, V., et al., "Map-Based Cloning of a Gene Controlling Omega-3 Fatty Acid Desaturation in *Arabidopsis*", Science, 1992, vol. 258, pp. 1353-1355.
Broadwater, J.A., et al., "Desaturation and Hydroxylation", The Journal of Biological Chemistry, 2002, vol. 277, No. 18, Issue of May 3, pp. 15613-15620.
Broun, P., et al., "Catalytic Plasticity of Fatty Acid Modification Enzymes Underlying Chemical Diversity of Plant Lipids", Science, 1998, vol. 282, pp. 1315-1317.
Calvo, A.M., et al., "Genetic Connection Between Fatty Acid Metabolism and Sporulation in *Aspergillus nidulans*", The Journal of Biological Chemistry, 2001, vol. 276, No. 28, Issue of Jul. 13, pp. 25766-25774.
Knutzon, D.S., et al., "Identification of 45-Desaturase from *Mortierella alpina* by Heterologous Expression in Bakers' Yeast and Canola", The Journal of Biological Chemistry, 1998, vol. 273, No. 45, Issue of Nov. 6, pp. 29360-29366.
Mantle, P.G., et al., "Differentiation of *Claviceps purpurea* in Axenic Culture", Journal of General Microbiology, 1976, vol. 93, pp. 321-334.
Mey, G. et al., "The Biotrophic, Non-Appressorium-Forming Grass pathogen *Claviceps purpurea* Needs a Fus3/Pmk1 Homologous Mitogen-Activated Protein Kinase for Colonization of Rye Ovarian Tissue", Molecular Plant Microbe Interactions, 2002, vol. 15, No. 4, pp. 303-312.
Okuley. J., et al., "*Arabidopsis* FAD2 Gene Encodes the Enzyme that is Essential for Polyunsaturated Lipid Synthesis", The Plant Cell, 1994, vol. 6, pp. 147-158.
Qi, B., et al.,"Production of Very Long Chain Polyunsaturated Omega-3 and Omega-6 Fatty Acids in Plants", Nature Biotechnology, 2004, vol. 22, No. 6, pp. 739-745.
Qiu, X., et al., "Identification of a Δ4 Fatty Acid Desaturase from *Thraustochytrium* sp. Involved in the Biosynthesis of Docasahexanoic Acid by Heterologous Expression in *Saccharomyces cerevisiae* and *Brassica juncea*", The Journal of Biological Chemistry, 2001, vol. 276, No. 34, Issue of Aug. 24, pp. 31561-31566.

(Continued)

*Primary Examiner* — Eileen B O Hara
(74) *Attorney, Agent, or Firm* — Drinker Biddle & Reath LLP

(57) ABSTRACT

The invention provides isolated nucleic acid molecules which encode novel fatty acid desaturases and elongases from the organism *Emiliana huxleyi*. The invention also provides recombinant expression vectors containing desaturase or elongase nucleic acid molecules, host cells into which the expression vectors have been introduced, and methods for large-scale production of long chain polyunsaturated fatty acids (LCPUFAs), e.g. arachidonic acid (ARA), eicosapentaenoic acid (EPA) or docosahexaenoic acid (DHA).

17 Claims, 13 Drawing Sheets

Specification includes a Sequence Listing.

(56) References Cited

OTHER PUBLICATIONS

Shanklin, J., et al., "Desaturation and Related Modifications of Fatty Acids", Annu. Rev. Plant Physiol. Plant Mol. Biol., 1998, vol. 49, pp. 611-641.
Soto, A.R., et al., "Identification and Preliminary Characterization of Two cDNAs Encoding Unique Carbonic Anhydrases from the Marine Alga *Emiliania huxleyi*", Applied and Environmental Microbiology, 2006, vol. 72, Issue 8, pp. 5500-5511.
Tudzynski, P. et al., "Biotechnology and Genetics of Ergot Alkaloids", Appl. Microbiol. Biotechnol., 2001, vol. 57, pp. 593-605.
International Search Report for PCT/EP2010/060178 dated Aug. 11, 2010.
International Preliminary Report on Patentability for PCT/EP2010/060178 dated Jan. 17, 2012.
Altschul, S., et al., "Gapped BLAST and PSI-BLAST: A New Generation of Protein Database Search Programs", Nucleic Acids Research, 1997, vol. 25, No. 17, pp. 3389-3402.
Bechtold, N., et al., "In Planta *agrobacterium* Mediated Gene Transfer by Infiltration of Adult *Arabidopsis thaliana* Plants", C. R. Acad. Sci. Ser. III Sci. Vie., 1993, vol. 316, pp. 1194-1199.
Becker, D., et al., "New Plant Binary Vectors with Selectable Markers Located Proximal to the Left T-DNA Border", Plant Molecular Biology, 1992, vol. 20, pp. 1195-1197.
Bevan, M., "Binary *Agrobacterium* Vectors for Plant Transformation", Nucleic Acids Research, 1984, vol. 12, No. 22, pp. 8711-8721.
Deblaere, R., et al., "Efficient Octopine Ti Plasmid-Derived Vectors for *Agrobacterium*-Mediated Gene Transfer to Plants", Nucleic Acids Research, 1985, vol. 13, No. 13, pp. 4777-4788.
Franck, A., et al., "Nucleotide Sequence of Cauliflower Mosaic Virus DNA", Cell, 1980, vol. 21, pp. 285-294.
Gielen, J., et al., "The Complete Nucleotide Sequence of the TL-DNA of the *Agrobacterium tumefaciens* Plasmid pTiAch5", The EMBO Journal, 1984, vol. 3, No. 4, pp. 835-846.
Lelievre, J., et al., "5'-CATGCAT-3' Elements Modulate the Expression of Glycinin Genes", Plant Physiol., 1992, vol. 98, pp. 387-391.
Michaelson, L. V., et al., "Functional Identification of a Fatty Acid $\Delta^5$ Desaturase Gene from *Caenorhabditis elegans*", FEBS Letters, 1998, vol. 439, pp. 215-218.
Napier, J. A., et al., "Genomic and Functional Characterization of Polyunsaturated Fatty Acid Biosynthesis in *Caenorhabditis elegans*", Lipids, 2001, vol. 36, No. 8, pp. 761-766.
Needleman, S. B., et al., "A General Method Applicable to the Search for Similarities in the Amino Acid Sequence of Two Proteins", J. Mol. Biol., 1970, vol. 48, pp. 443-453.
Sayanova, O., et al., "Mutagenesis and Heterologous Expression in Yeast of a Plant $\Delta^6$-Fatty Acid Desaturase", Journal of Experimental Botany, 2001, vol. 52, No. 360, pp. 1581-1585.
Sperling, P., et al., "Functional Identification of a $D^8$-Sphingolipid Desaturase from *Borago officinalis*", Archives of Biochemistry and Biophysics, 2001, vol. 388, No. 2, pp. 293-298.
Stockhaus, J., et al., "Correlation of the Expression of the Nuclear Photosynthetic Gene ST-LS1 with the Presence of Chloroplasts", The EMBO Journal, 1989, vol. 8, No. 9, pp. 2445-2451.

\* cited by examiner

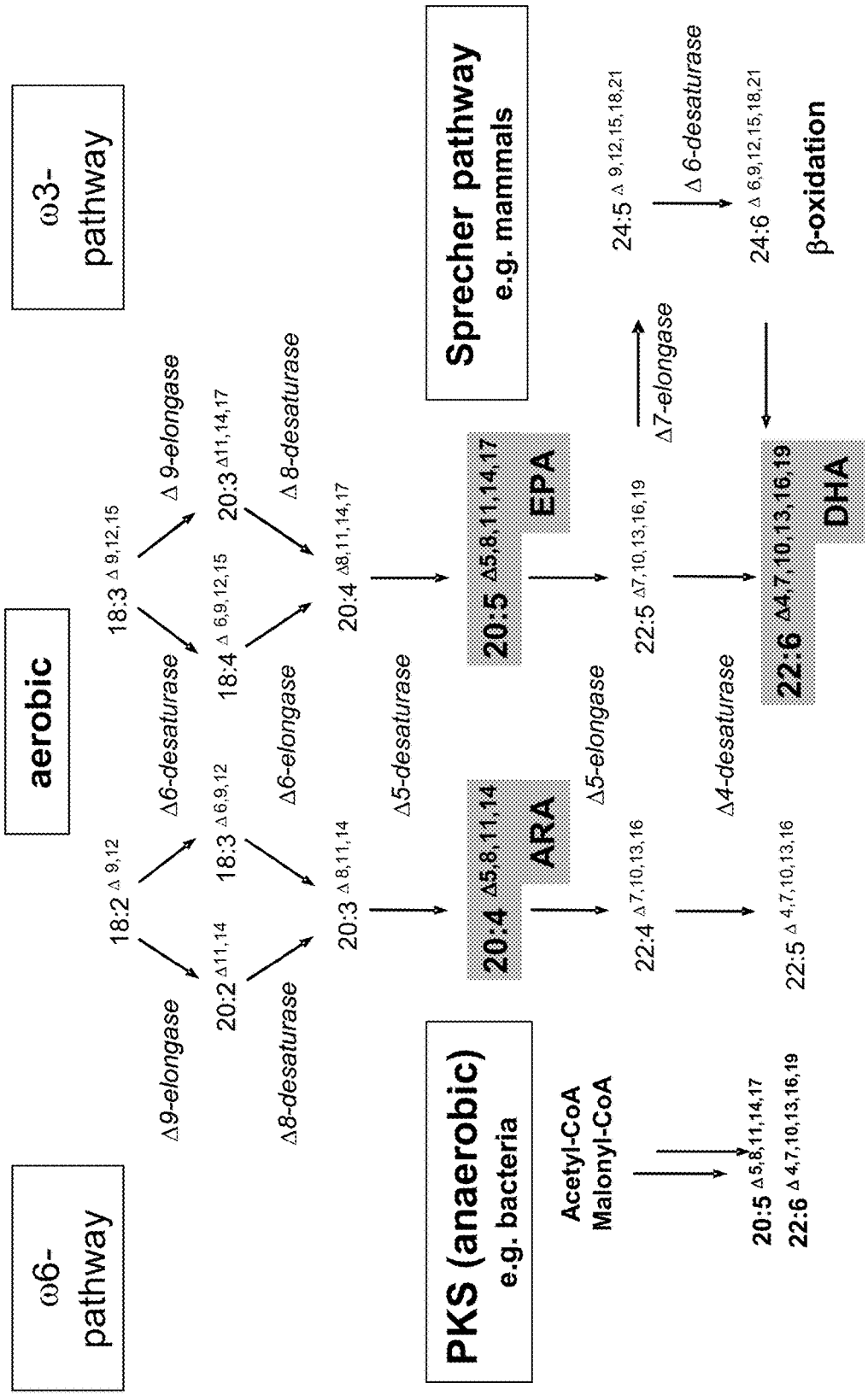
Figure 1 : Schematical figure of the different enzymatic activities leading to the production of ARA, EPA and DHA.

Figure 2 : Gas chromatograph of yeast expression experiment with feeding of 22:5n-3 in the presence (A) and absence (B) of d4Des(Eh). The arrow indicates the formation of 22:6, the product of d4Des(Eh) activity.
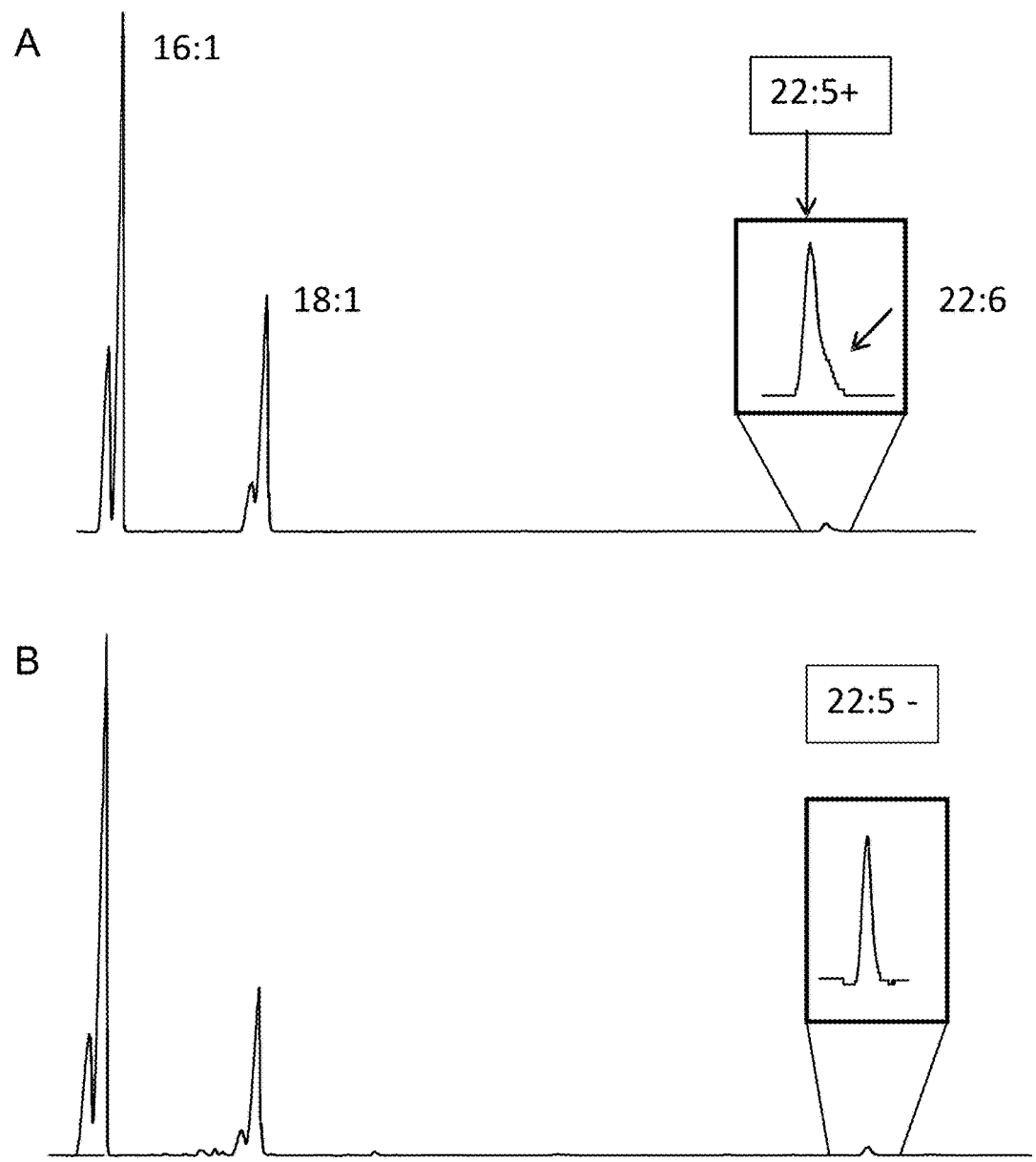

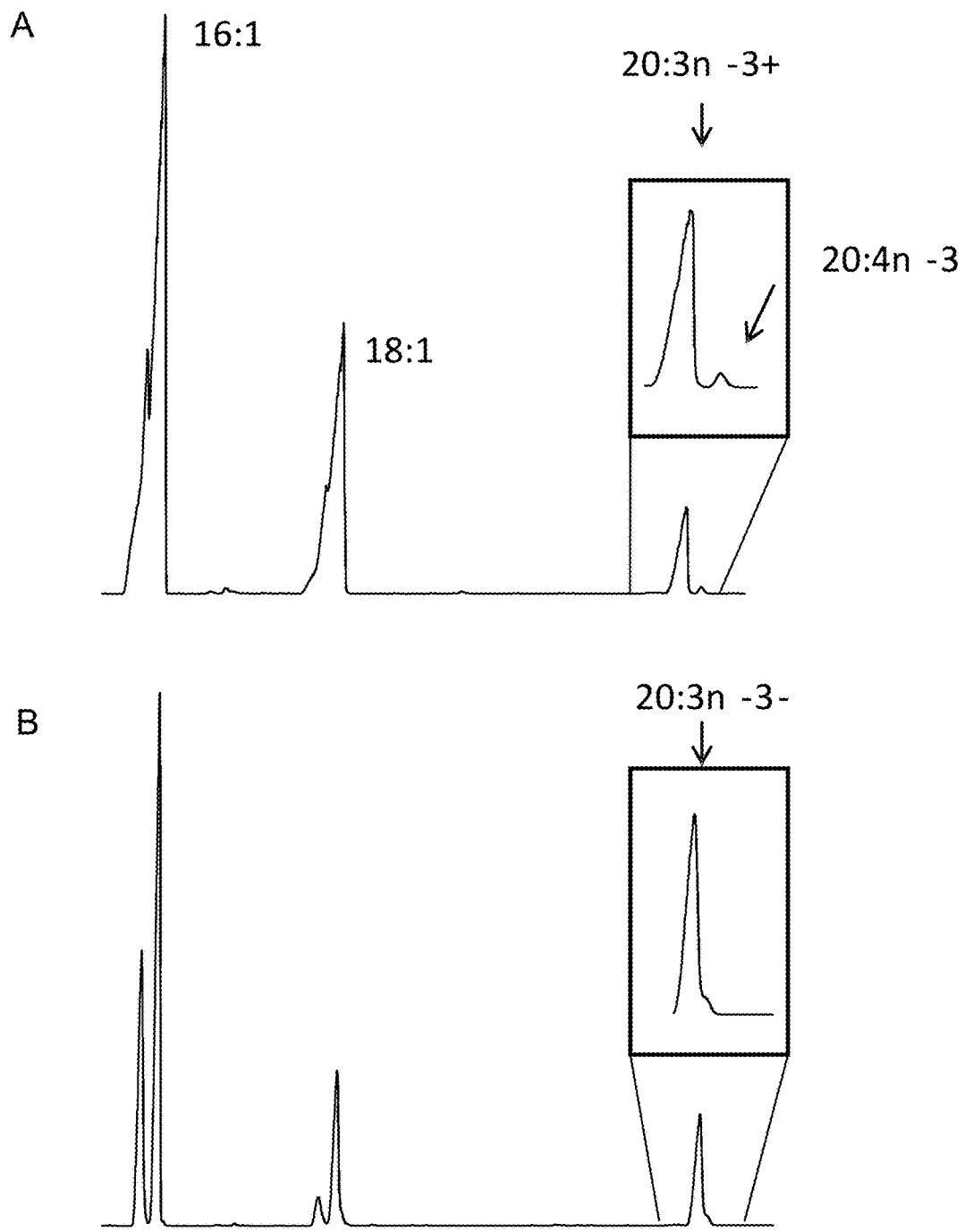
Figure 3 : Gas chromatograph of yeast expression experiment with feeding of 20:3n-3 in the presence (A) and absence (B) of d8Des(Eh). The arrow indicates the formation of 20:4n-3, the product of d8Des(Eh) activity.

Figure 4 : Gas chromatograph of yeast expression experiment with feeding of 18:3n-3 (ALA) in the presence (A) and absence (B) of d9Elo(Eh). The arrow indicates the formation of 20:3n-3, the product of d9Elo(Eh) activity.
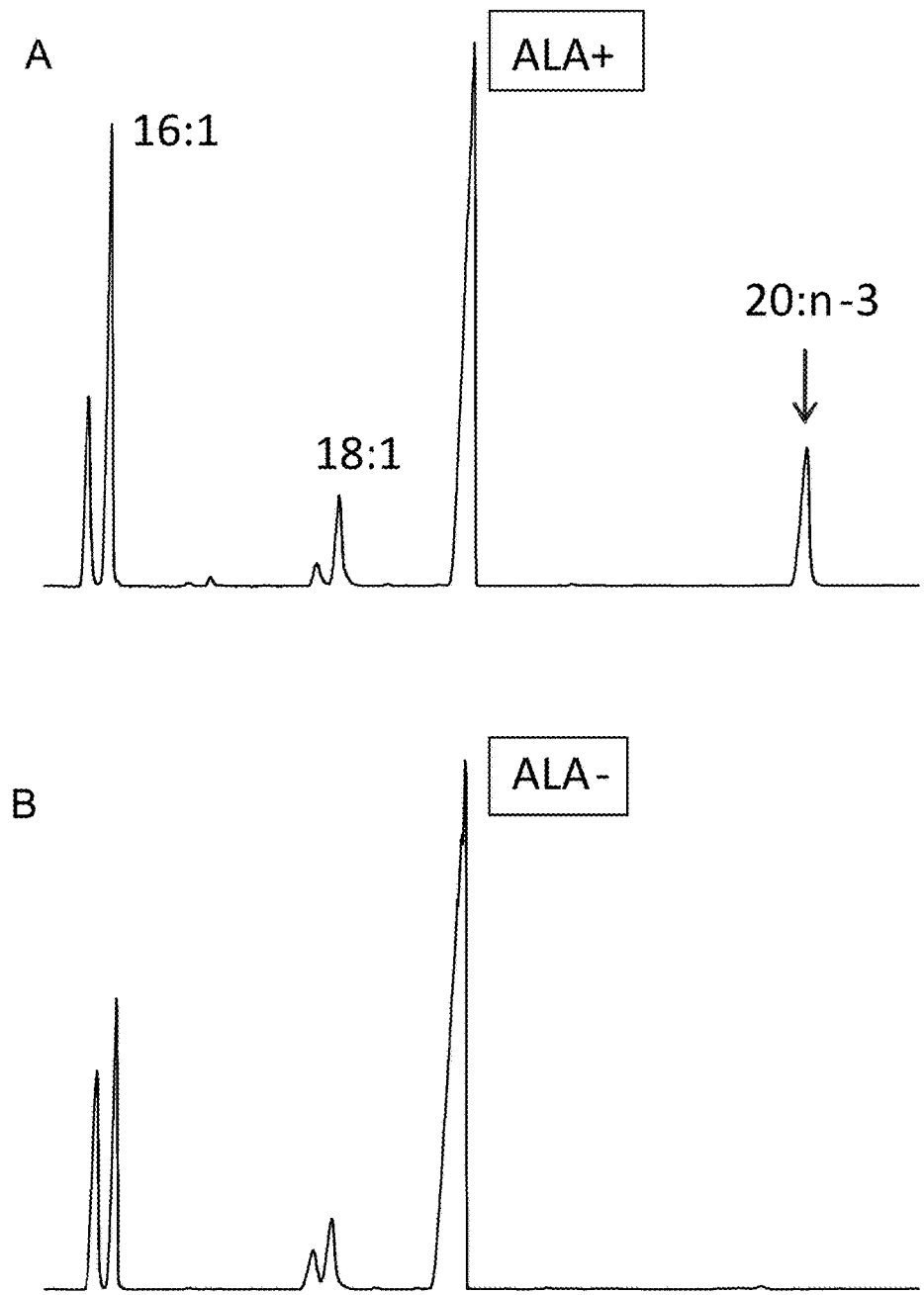

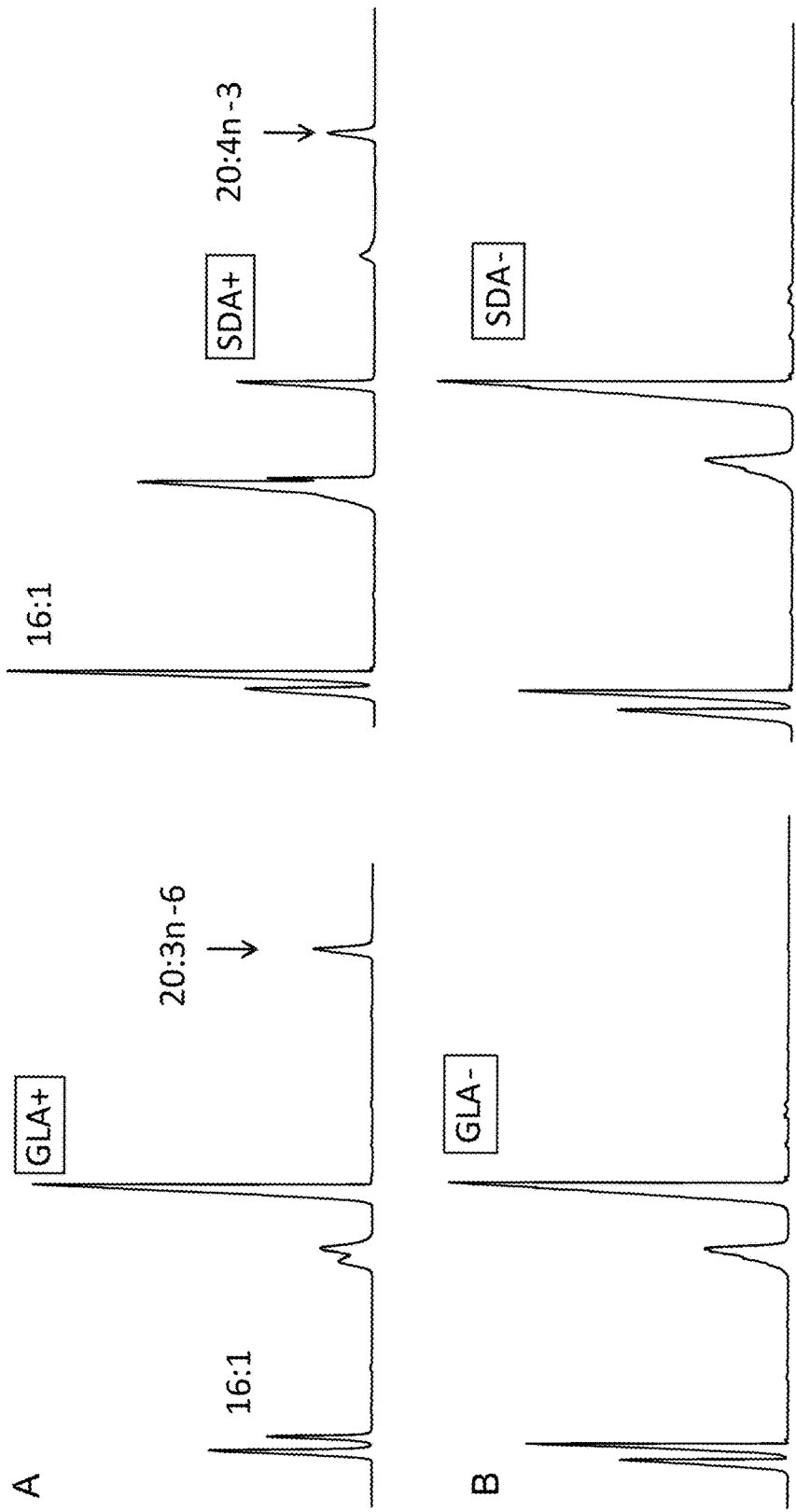
Figure 5 : Gas chromatograph of yeast expression experiment with feeding of 18:3n-6 (GLA) and 18:4n-3 (SDA) in the presence (A) and absence (B) of d5Elo(Eh). The arrow indicates the formation of 20:3n-6 or 20:4n-3, respectively, the products of d5Elo(Eh) activity

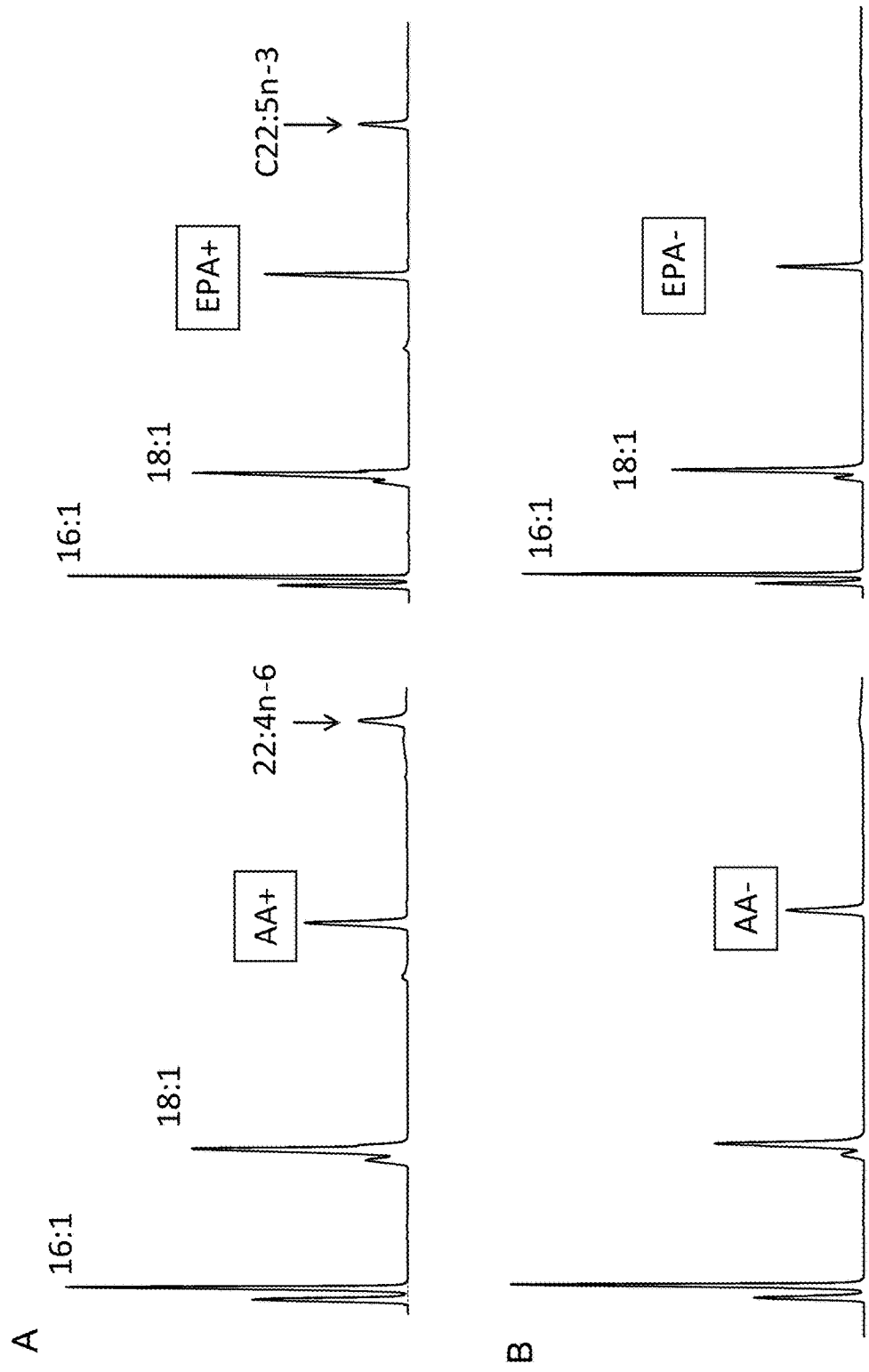
Figure 6: Gas chromatograph of yeast expression experiment with feeding of 20:4n-6 (ARA) and 20:5n-3 (EPA) in the presence (A) and absence (B) of d5Elo(Eh). The arrow indicates the formation of 22:4n-6 or 22:5n-3, respectively, the products of d5Elo(Eh) activity.

Figure 7 : Gas chromatograph analysis of mature Arabidopsis seeds. Peaks were quantified and listed in the table below. EmiElo91 and EmiElo92 are two selected events transformed with d9Elo(Eh). WT is a non-transformed control. The products of d9Elo(Eh) activity are 20:2 and 20:3n3, which are 10fold increased compared to the levels of the non-transformed control.

| Fatty acids | 16:0 | 18:0 | 18:1 | 18:2 | ALA | 18:4 | 20:0 | 20:1 | 20:2 | 20:3n3 | 22:1 |
|---|---|---|---|---|---|---|---|---|---|---|---|
| EmiElo91 | 4.64 | 3.43 | 13.34 | 23.88 | 12.64 | 0.18 | 2.55 | 22 | 11.26 | 3.73 | 1.69 |
| EmiElo92 | 4.21 | 3.04 | 12.63 | 24.63 | 14.57 | 0.34 | 2.28 | 21.56 | 10.94 | 4.02 | 1.8 |
| WT | 6.22 | 3.21 | 16.17 | 27.75 | 16.63 | 0.16 | 2.4 | 22.2 | 1.95 | 0.46 | 2.15 |

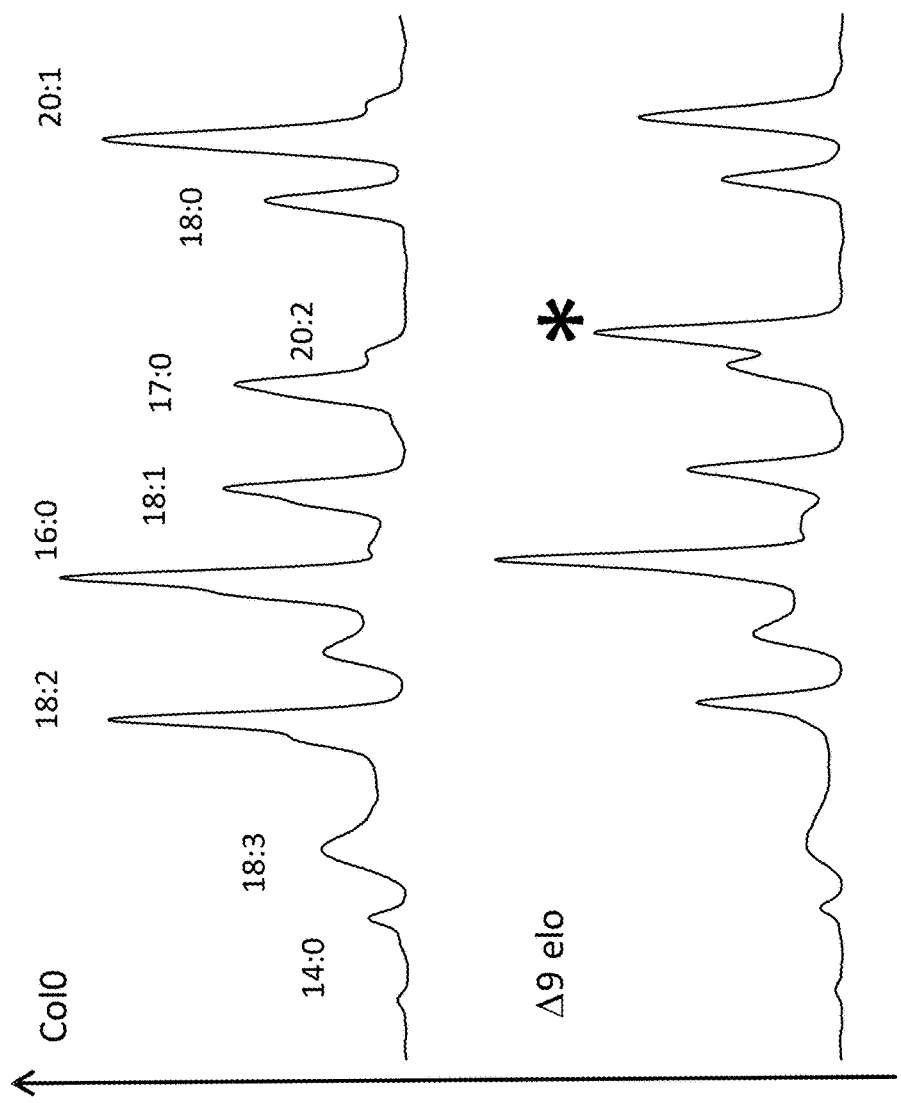
Figure 8 : Acyl-CoA analysis of mature Arabidopsis seeds of event EmiElo91 transformed with d9Elo(Eh). Col0 is seed material from a non-transformed plant. Δ9elo is seed material from EmiElo91. The product of d9Elo(Eh) activity is marked with a star (20:2), which is massively increased compared to the control, indicating the functional expression of d9Elo(Eh).

Figure 9 : Gas chromatographic analysis of mature *Arabidopsis* seeds transformed with the construct AP2 (gene combinations d9Elo(Eh)_d8Des(Eh)_d5Des(Eh)_d12Des(Ps)_o3Des(Pi). Peaks were quantified and listed in the table below. The products of d9Elo(Eh) activity are 20:2 and 20:3n3.

| FA | 16:0 | 18:0 | 18:1c9 | 18:1c11 | 18:2 | 18:3n3 | 20:0 | 20:1 | 20:2 | 20:3n3 |
|---|---|---|---|---|---|---|---|---|---|---|
| AP2 1 | 6.5 | 3.4 | 12.9 | 1.8 | 27.4 | 13.2 | 2.0 | 15.9 | 7.5 | 4.5 |
| AP2 5 | 5.7 | 3.2 | 14.9 | 1.5 | 26.4 | 13.1 | 2.0 | 17.9 | 6.8 | 3.2 |
| AP2 11 | 5.9 | 3.2 | 13.5 | 1.6 | 26.6 | 13.3 | 2.0 | 17.1 | 7.7 | 4.0 |
| AP2 16 | 6.5 | 3.1 | 11.9 | 1.7 | 26.9 | 13.5 | 2.0 | 16.2 | 7.8 | 5.0 |
| AP2 17 | 7.6 | 3.4 | 12.2 | 3.1 | 30.6 | 13.8 | 2.0 | 14.9 | 3.8 | 2.2 |
| AP2 18 | 6.5 | 3.3 | 11.4 | 1.9 | 27.2 | 14.2 | 2.3 | 16.7 | 6.7 | 3.9 |
| AP2 21 | 6.6 | 3.1 | 10.9 | 1.8 | 24.9 | 15.5 | 2.2 | 15.9 | 7.4 | 5.7 |
| AP2 22 | 6.2 | 3.2 | 9.7 | 1.7 | 25.9 | 14.4 | 2.1 | 15.9 | 8.7 | 6.4 |
| AP2 23 | 6.3 | 3.1 | 10.8 | 1.9 | 27.1 | 14.6 | 2.1 | 16.0 | 7.5 | 5.2 |
| AP2 24 | 5.9 | 3.1 | 10.3 | 1.6 | 25.4 | 14.2 | 2.1 | 16.1 | 9.4 | 5.9 |
| AP2 25 | 6.2 | 3.0 | 12.0 | 1.6 | 26.0 | 14.8 | 2.0 | 17.1 | 7.7 | 3.9 |
| AP2 26 | 6.2 | 3.3 | 11.1 | 1.8 | 26.6 | 13.1 | 2.1 | 16.0 | 8.6 | 5.7 |
| AP2 27 | 5.8 | 3.1 | 9.8 | 2.0 | 24.1 | 12.2 | 2.2 | 15.8 | 9.5 | 8.6 |
| AP2 28 | 6.0 | 3.2 | 9.8 | 1.8 | 25.0 | 13.0 | 2.2 | 15.7 | 8.9 | 7.6 |
| AP2 29 | 6.6 | 3.3 | 10.1 | 2.0 | 26.5 | 14.1 | 2.2 | 15.8 | 7.9 | 5.8 |
| AP2 30 | 5.6 | 3.0 | 10.7 | 1.5 | 26.7 | 13.2 | 2.0 | 16.6 | 10.5 | 4.7 |
| AP2 31 | 5.5 | 3.2 | 11.2 | 1.8 | 24.5 | 12.6 | 2.1 | 16.5 | 10.6 | 6.0 |
| AP2 32 | 5.7 | 3.2 | 11.1 | 1.6 | 25.5 | 13.5 | 2.2 | 17.4 | 8.8 | 4.9 |
| AP2 33 | 6.5 | 3.2 | 9.2 | 1.9 | 26.7 | 15.4 | 2.3 | 15.8 | 7.6 | 5.5 |
| AP2 34 | 6.4 | 3.3 | 10.1 | 2.0 | 26.1 | 13.7 | 2.3 | 16.7 | 8.0 | 5.7 |
| AP2 42 | 5.7 | 3.4 | 13.1 | 1.8 | 25.6 | 12.8 | 2.3 | 18.0 | 7.6 | 4.2 |
| AP2 46 | 6.3 | 3.3 | 10.3 | 2.4 | 27.2 | 12.8 | 2.4 | 17.0 | 6.7 | 5.0 |
| AP2 47 | 5.7 | 3.5 | 13.3 | 2.0 | 26.7 | 12.4 | 2.3 | 17.5 | 7.3 | 3.8 |
| AP2 48 | 5.6 | 3.5 | 12.0 | 2.0 | 25.5 | 12.2 | 2.3 | 16.6 | 8.9 | 5.7 |
| AP2 49 | 6.0 | 2.9 | 12.9 | 1.6 | 26.7 | 14.2 | 2.2 | 18.4 | 6.5 | 3.2 |
| AP2 50 | 5.8 | 3.0 | 10.8 | 2.5 | 26.6 | 13.9 | 2.2 | 17.1 | 6.7 | 5.1 |
| average | 6.1 | 3.2 | 11.4 | 1.9 | 26.3 | 13.6 | 2.2 | 16.6 | 7.9 | 5.1 |
| std | 0.5 | 0.2 | 1.4 | 0.3 | 1.2 | 0.9 | 0.1 | 0.8 | 1.4 | 1.4 |

Figure 10

| FA | 16:0 | 18:0 | 18:1 Δ9 | 18:1 Δ11 | 18:2 Δ9,12 | GLA 18:3n6 | 18:4 | 20:0 | 20:1 Δ11 | 20:2 Δ11,14 | DHGLA 20:3n6 | ARA 20:4n3 | 20:3n3 | ETA 20:4n3 | EPA 20:5n3 | 22:0 | 22:1 | DPA 22:5 | DHA 22:6 |
|---|---|---|---|---|---|---|---|---|---|---|---|---|---|---|---|---|---|---|---|
| OstELO5EmD4_1 | 6. | 3. | 10. | 1.9 | 25.5 | 0.7 | 0.3 | 2. | 17.9 | 2.0 | 0 | 1 | 0. | 1 | 2 | 0. | 1. | 1 | 2.3 |
| OstELO5EmD4_2 | 7. | 3. | 13. | 2.4 | 27.4 | 2.7 | 1.5 | 2. | 16.0 | 1.1 | 0 | 0 | 0. | 0 | 1 | 0. | 1. | 0 | 1.2 |
| OstELO5EmD4_3 | 6. | 3. | 10. | 2.3 | 26.2 | 1.9 | 1.0 | 2. | 15.5 | 1.4 | 0 | 1 | 0. | 0 | 3 | 0. | 1. | 0 | 2.7 |
| OstELO5EmD4_4 | 7. | 3. | 8.7 | 2.8 | 23.7 | 5.7 | 3.2 | 2. | 15.2 | 1.1 | 0 | 0 | 1. | 0 | 2 | 0. | 1. | 0 | 1.6 |
| OstELO5EmD4_5 | 7. | 3. | 10. | 2.4 | 24.6 | 3.2 | 1.8 | 2. | 16.3 | 1.1 | 0 | 0 | 0. | 0 | 2 | 0. | 1. | 0 | 2.0 |
| OstELO5EmD4_6 | 8. | 3. | 9.0 | 2.2 | 23.2 | 6.1 | 4.0 | 2. | 15.7 | 1.3 | 0 | 0 | 0. | 1 | 1 | 0. | 1. | 0 | 1.4 |
| OstELO5EmD4_7 | 7. | 3. | 7.9 | 2.2 | 24.0 | 1.0 | 0.7 | 2. | 14.6 | 2.1 | 0 | 1 | 1. | 1 | 3 | 0. | 1. | 1 | 4.7 |
| OstELO5EmD4_8 | 9. | 3. | 10. | 1.7 | 26.8 | 1.1 | 0.5 | 1. | 13.7 | 1.6 | 0.7 | 1 | 0. | 1 | 2 | 0. | 1. | 0 | 2. |
| OstELO5EmD4_14 | 8. | 3. | 12. | 1.6 | 25.4 | 4.8 | 2. | 2. | 15.7 | 1.2 | 0.1 | 0 | 0. | 0 | 0 | 0. | 1. | 0 | 0. |
| OstELO5EmD4_15 | 9. | 3. | 11. | 1.7 | 25.8 | 3.9 | 2. | 1. | 13.6 | 1.2 | 0.1 | 0 | 0. | 0 | 2 | 0. | 0. | 0 | 1. |
| OstELO5EmD4_16 | 7. | 3. | 9.7 | 2.2 | 24.3 | 6.7 | 3. | 2. | 14.2 | 0.9 | 0.1 | 0 | 0. | 0 | 0 | 0. | 1. | 0 | 1. |
| OstELO5EmD4_18 | 7. | 3. | 10. | 2.1 | 24.4 | 5.1 | 3. | 2. | 15.7 | 1.3 | 0.5 | 1 | 0. | 0 | 2 | 0. | 1. | 0 | 1. |
| OstELO5EmD4_20 | 6. | 3. | 8.8 | 2.0 | 24.4 | 1.0 | 0. | 2. | 16.5 | 1.8 | 0.7 | 0 | 0. | 1 | 3 | 0. | 1. | 0 | 3. |
| OstELO5EmD4_21 | 5. | 3. | 11. | 2.0 | 26.4 | 0.6 | 0. | 2. | 18.3 | 1.9 | 0.7 | 0 | 0. | 0 | 2 | 0. | 1. | 0 | 1. |
| OstELO5EmD4_25 | 6. | 3. | 10. | 1.9 | 24.9 | 2.1 | 1. | 2. | 17.4 | 1.9 | 0.5 | 0 | 0. | 0 | 1 | 0. | 1. | 0 | 1. |
| OstELO5EmD4_26 | 6. | 3. | 11. | 2.1 | 25.5 | 5.0 | 3. | 2. | 15.6 | 1.3 | 0.2 | 1 | 0. | 0 | 1 | 0. | 1. | 0 | 1. |
| OstELO5EmD4_27 | 6. | 3. | 12. | 1.9 | 24.2 | 4.2 | 2. | 2. | 16.4 | 1.3 | 0.4 | 0 | 0. | 0 | 2 | 0. | 1. | 0 | 2. |
| OstELO5EmD4_28 | 8. | 3. | 8.2 | 2.4 | 23.5 | 3.7 | 2. | 2. | 14.2 | 1.1 | 0.8 | 1 | 1. | 1 | 4 | 0. | 1. | 1 | 3. |
| OstELO5EmD4_101 | 6. | 3. | 8.2 | 2.1 | 23.1 | 1.4 | 0. | 3. | 17.4 | 1.7 | 0.6 | 0 | 1. | 1 | 3 | 0. | 1. | 1 | 1. |
| OstELO5EmD4_103 | 6. | 3. | 10. | 2.2 | 26.7 | 1.1 | 0. | 2. | 17.1 | 2.0 | 0.2 | 0 | 0. | 0 | 1 | 0. | 1. | 0 | 3. |
| OstELO5EmD4_104 | 6. | 3. | 9.2 | 2.4 | 25.3 | 1.2 | 0. | 2. | 15.9 | 1.6 | 0.7 | 1 | 1. | 1 | 4 | 0. | 1. | 1 | 3. |
| OstELO5EmD4_105 | 6. | 3. | 9.3 | 2.0 | 24.9 | 3.5 | 1. | 2. | 15.1 | 1.4 | 0.7 | 2 | 0. | 0 | 3 | 0. | 1. | 1 | 2. |
| OstELO5EmD4_106 | 7. | 3. | 7.2 | 2.3 | 19.5 | 3.1 | 2. | 2. | 13.8 | 1.3 | 0.4 | 1 | 1. | 1 | 7 | 0. | 1. | 2 | 4. |
| OstELO5EmD4_109 | 7. | 3. | 7.5 | 2.4 | 21.7 | 1.8 | 1. | 2. | 14.7 | 1.7 | 0.3 | 0 | 1. | 0 | 5 | 0. | 1. | 1 | 4. |
| OstELO5EmD4_111 | 7. | 3. | 10. | 2.2 | 25.6 | 2.5 | 1. | 2. | 14.5 | 1.3 | 0.3 | 1 | 0. | 0 | 3 | 0. | 1. | 1 | 2. |
| OstELO5EmD4_112 | 7. | 3. | 6.3 | 3.5 | 20.1 | 2.1 | 1. | 2. | 13.3 | 1.7 | 1.0 | 0 | 1. | 2 | 6 | 0. | 1. | 1 | 3. |
| OstELO5EmD4_115 | 8. | 3. | 7.8 | 2.7 | 24.1 | 2.6 | 1. | 2. | 13.8 | 1.5 | 0.3 | 1 | 1. | 0 | 4 | 0. | 1. | 2 | 3. |
| OstELO5EmD4_116 | 7. | 3. | 10. | 2.5 | 24.8 | 5.7 | 3. | 2. | 13.7 | 0. | 0.2 | 0 | 1.0 | 0 | 2 | 0. | 1. | 0 | 1. |
| OstELO5EmD4_117 | 6. | 3. | 9. | 2. | 26. | 1. | 0. | 2. | 15.2 | 1. | 0.9 | 1 | 1.3 | 1 | 3 | 0. | 1. | 1 | 3. |
| OstELO5EmD4_118 | 6. | 3. | 10.4 | 2. | 23. | 3. | 2. | 2. | 15.3 | 1. | 1.2 | 0 | 1.1 | 2 | 3 | 0. | 1. | 1 | 1. |
| OstELO5EmD4_119 | 7. | 3. | 9. | 2. | 25. | 4. | 2. | 2. | 14.2 | 1. | 0.2 | 0 | 1.0 | 0 | 2 | 0. | 0. | 0 | 2. |
| OstELO5EmD4_120 | 6. | 3. | 10.0 | 2. | 27. | 1. | 0. | 2. | 15.1 | 1. | 0.8 | 1 | 0.9 | 1 | 2 | 0. | 1. | 1 | 2. |
| average | 7. | 3. | 9. | 2.2 | 24. | 3.0 | 1. | 2. | 15.4 | 1. | 0. | 0. | 1.0 | 0. | 3. | 0.4 | 1.3 | 1. | 2. |
| std | 0. | 0. | 1. | 0.4 | 1. | 1.8 | 1. | 0. | 1. | 0 | 0 | 0. | 0.2 | 0. | 1. | 0.1 | 0.2 | 0. | 1. |

| Line | 16: | 18: | 18: | 18:n-6 | GL | 18:n-3 | SD | 20:n-9 | A | EP | DP | DH |
|---|---|---|---|---|---|---|---|---|---|---|---|---|
| BBC | 3.9 | 4.1 | 9.9 | 21.0 | 1.0 | 10.5 | 0.6 | 22. | 1.6 | 10. | - | - |
| OstELO TcD4 | 6.2 | 3.8 | 6.2 | 21.8 | 2.0 | 11.6 | 1.1 | 14. | 1.5 | 5.4 | 4.4 | 3.8 |
| OstELO EmD4 | 7.1 | 3.3 | 7.9 | 24.0 | 1.0 | 13.6 | 0.7 | 14. | 1.2 | 3.8 | 1.6 | 4.7 |
| BBC-OTElo5-EhD4-2 | 6.9 | 3.2 | 7.1 | 21.5 | 1.2 | 11.8 | 0.6 | 13. | 1.3 | 4.6 | 8.5 | 0.2 |

Figure 11 : Gas chromatographic analysis of mature *Arabidopsis* seeds transformed with different constructs. Values are generated from the best individual *Arabidopsis* line. Following constructs are compared: BBC, OstELO5TcD4 and OstELO5EmD4. The construct with d4Des(Eh) delivered highest levels of DHA and highest ratio of DHA:DPA (2,9).

Figure 12 : Gas chromatographic analysis of mature *Arabidopsis* seeds transformed with the construct EmELO5Tcd4. The production of 22:5 and 22:6 demonstrate the activity of d5Elo(Eh) in seeds.

| FA | 16:0 | 18:0 | 18:1 Δ9 | 18:1 Δ11 | 18:2 Δ9,12 | GLA 18:3n6 | ALA 18:3n3 | 18:4 | 20:0 | 20:1 Δ11 | 20:1 Δ13 | 20:2 Δ11,14 | DHGLA 20:3n6 | ARA 20:4n6 | 20:3n3 | ETA 20:4n3 | EPA 20:5n3 | 22:1 | DPA 22:5 | DHA 22:6 |
|---|---|---|---|---|---|---|---|---|---|---|---|---|---|---|---|---|---|---|---|---|
| EmELO5Tcd4_1 | 6.5 | 3.4 | 10.5 | 2.5 | 24.2 | 3.3 | 12.7 | 2.0 | 2.3 | 17.5 | 3.3 | 1.4 | 0.2 | 0.5 | 1.0 | 0.5 | 4.1 | 1.7 | 0.2 | 0.2 |
| EmELO5Tcd4_2 | 6.4 | 3.6 | 10.0 | 1.9 | 25.2 | 3.1 | 13.1 | 1.8 | 2.3 | 16.1 | 2.4 | 1.4 | 0.2 | 1.0 | 1.2 | 0.5 | 5.6 | 1.3 | 0.2 | 0.2 |
| EmELO5Tcd4_3 | 6.1 | 3.5 | 14.3 | 1.8 | 27.0 | 0.0 | 16.8 | 0.0 | 2.5 | 18.4 | 2.3 | 3.6 | 0.0 | 0.0 | 1.6 | 0.0 | 0.0 | 1.6 | 0.0 | 0.0 |
| EmELO5Tcd4_4 | 7.0 | 3.6 | 10.1 | 2.4 | 26.2 | 3.4 | 11.9 | 2.1 | 2.3 | 15.9 | 2.9 | 1.1 | 0.3 | 0.6 | 1.2 | 0.5 | 4.3 | 1.2 | 0.3 | 0.4 |
| EmELO5Tcd4_5 | 6.3 | 3.5 | 8.3 | 2.1 | 23.1 | 1.5 | 12.0 | 0.8 | 2.2 | 15.6 | 2.7 | 1.4 | 1.1 | 1.3 | 1.4 | 2.5 | 8.7 | 1.2 | 0.2 | 0.3 |
| EmELO5Tcd4_6 | 6.1 | 3.6 | 10.6 | 2.1 | 24.9 | 1.6 | 13.3 | 0.8 | 2.3 | 16.6 | 2.5 | 1.8 | 0.9 | 0.7 | 1.3 | 1.7 | 4.8 | 1.3 | 0.2 | 0.2 |
| EmELO5Tcd4_7 | 5.5 | 3.4 | 10.3 | 1.8 | 25.7 | 0.5 | 12.6 | 0.2 | 2.5 | 18.2 | 2.3 | 2.0 | 0.9 | 1.4 | 1.1 | 1.4 | 6.0 | 1.5 | 0.2 | 0.3 |
| average | 6.3 | 3.5 | 10.6 | 2.1 | 25.2 | 1.9 | 13.2 | 1.1 | 2.4 | 16.9 | 2.6 | 1.8 | 0.5 | 0.8 | 1.2 | 1.0 | 4.8 | 1.4 | 0.2 | 0.2 |
| std | 0.5 | 0.1 | 1.8 | 0.3 | 1.3 | 1.4 | 1.7 | 0.9 | 0.1 | 1.1 | 0.4 | 0.9 | 0.4 | 0.5 | 0.2 | 0.9 | 2.6 | 0.2 | 0.1 | 0.1 |

Figure 13: Gas chromatographic analysis of mature *Arabidopsis* seeds transformed with four different constructs (A). The production of ARA and EPA demonstrates the activity of d5Des(Eh) in seeds (B). It could be shown that d5Des(Eh) has a preference for n-6 fatty acids (ARA).
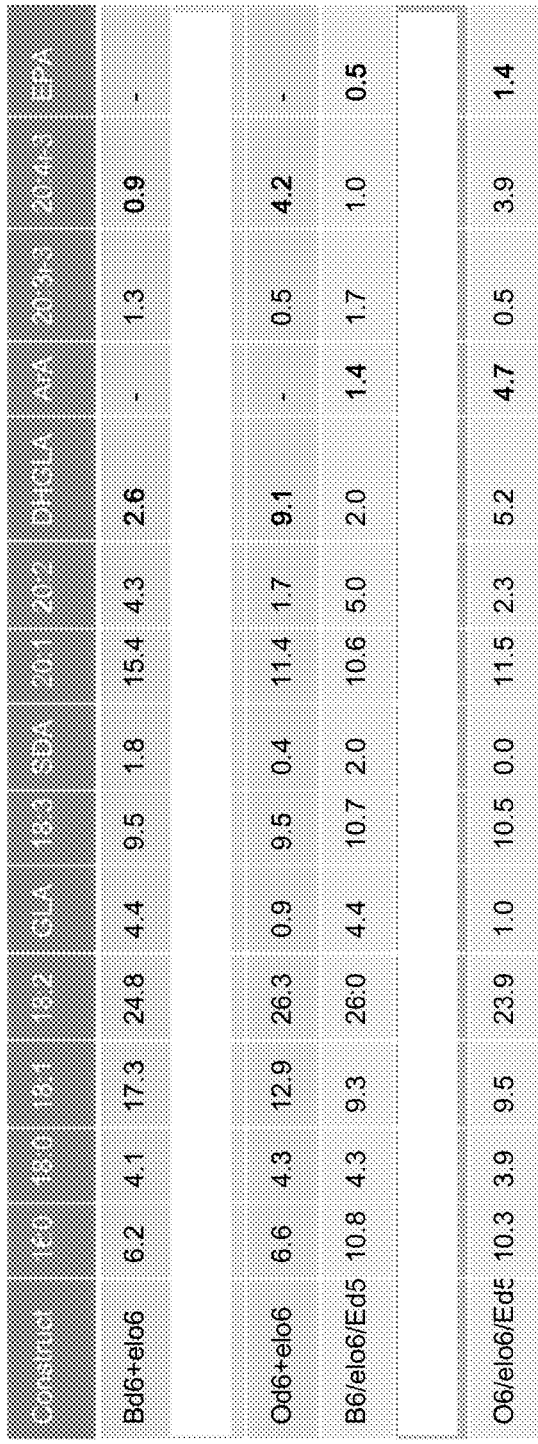

USES OF NOVEL FATTY ACID DESATURASES AND ELONGASES AND PRODUCTS THEREOF

RELATED APPLICATIONS

This application is a continuation of U.S. application Ser. No. 13/384,277 filed Jan. 16, 2012, now U.S. Pat. No. 9,493,520, which is a national stage application (under 35 U.S.C. § 371) of PCT/EP2010/060178, filed Jul. 15, 2010, which claims benefit of U.S. Provisional Application No. 61/226,301, filed Jul. 17, 2009, and European Application No. 09165752.8, filed Jul. 17, 2009. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074021_0167_01. The size of the text file is 58 KB, and the text file was created on Nov. 15, 2016.

The invention in principle pertains to the field of recombinant manufacture of fatty acids. It provides nucleic acid molecules which encode novel fatty acid desaturases and elongases. The invention also provides recombinant expression vectors containing desaturase and elongase nucleic acid molecules, host cells into which the expression vectors have been introduced, and methods for large-scale production of long chain polyunsaturated fatty acids (LCPUFAs), e.g. arachidonic acid (ARA), eicosapentaenoic acid (EPA) or docosahexaenoic acid (DHA).

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al, (1997) Am. J. Clin. Nutr. 66:1032S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citiziens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and ARA are both 45 essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from AA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

A large number of beneficial health effects have been shown for DHA or mixtures of EPA/DHA. DHA is a n-3 very long chain fatty acid with six double bonds.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

Thus, the present invention relates to a polynucleotide comprising a nucleic acid sequence elected from the group consisting of:
a) a nucleic acid sequence having a nucleotide sequence as shown in SEQ ID NOs: 1, 3, 5, 7 or 9;
b) a nucleic acid sequence encoding a polypeptide having an amino acid sequence as shown in SEQ ID NOs: 2, 4, 6, 8 or 10;
c) a nucleic acid sequence being at least 70% identical to the nucleic acid sequence of a) or b), wherein said nucleic acid sequence encodes a polypeptide having desaturase or elongase activity;
d) a nucleic acid sequence encoding a polypeptide having desaturase or elongase activity and having an amino acid sequence which is at least 82% identical to the amino acid sequence of any one of a) to c); and
e) a nucleic acid sequence which is capable of hybridizing under stringent conditions to any one of a) to d), wherein said nucleic acid sequence encodes a polypeptide having desaturase or elongase activity.

The term "polynucleotide" as used in accordance with the present invention relates to a polynucleotide comprising a nucleic acid sequence which encodes a polypeptide having desaturase or elongase activity. Preferably, the polypeptide encoded by the polynucleotide of the present invention having desaturase or elongase activity upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the present state of the art set of desaturases and elongases required for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to the said control. Preferably, the LCPUFA referred to before is a polyunsaturated fatty acid having a C-20 or C-22 fatty acid body, more preferably, ARA, EPA or DHA. Suitable assays for measuring the activities mentioned before are described in the accompanying Examples.

The term "desaturase" or "elongase" as used herein refers to the activity of a desaturase, introducing a double bond into the carbon chain of a fatty acid, preferably into fatty acids with 18, 20 or 22 carbon molecules, or an elongase, introducing two carbon molecules into the carbon chain of a fatty acid, preferably into fatty acids with 18, 20 or 22 carbon molecules More preferably, polynucleotides having a nucleic acid sequence as shown in SEQ ID NOs: 1, 3, 5, 7 or 9 encoding polypeptides having amino acid sequences as shown in SEQ ID NOs: 2, 4, 6, 8 or 10 or variants thereof, preferably, exhibit desaturase or elongase activity.

Polynucleotides encoding a polypeptide having desaturase or elongase activity as specified above has been obtained in accordance with the present invention, preferably, from *Emiliana huxleyi*. However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from *Euteleostomi, Actinopterygii; Neopterygii; Teleostei; Euteleostei, Protacanthopterygii, Salmoniformes; Salmonidae* or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thallasiosira* or *Phaeodactylum*.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 1, 3, 5, 7 or 9 or by a polynucleotide encoding a polypeptide having an amino acid sequence as shown in any one of SEQ ID NOs: 2, 4, 6, 8 or 10 by at least one nucleotide substitution, addition and/or deletion, whereby the variant nucleic acid sequence shall still encode a polypeptide having a desaturase or elongase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the above-mentioned buffer, for example 50% formamide, the temperature under standard conditions is approximately 42° C. The hybridization conditions for DNA:DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The above-mentioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid sequences shown in any one of SEQ ID NOs: 1, 3, 5, 7 or 9, preferably, encoding polypeptides retaining a desaturase or elongase activity as specified above. Moreover, also encompassed are polynucleotides which comprise nucleic acid sequences encoding a polypeptide having an amino acid sequences which are at least 50%, at least 55%, at least 60%, at least 65%, at least 70%, at least 75%, at least 80%, at least 85%, at least 90%, at least 95%, at least 98% or at least 99% identical to the amino acid sequences shown in any one of SEQ ID NOs: 2, 4, 6, 8 or 10, wherein the polypeptide, preferably, retains desaturase or elongase activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (*EMBOSS: The European Molecular Biology Open Software Suite*, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap entension penalty of 0.5, 1, 2, 3, 4, 5, or 6. Guides for local installation of the EMBOSS package as well as links to WEB-Services can be found at emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using acyltransferase nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to acyltransferase sequences of the invention. BLAST using acyltransferase protein sequences of the invention as query sequence can be performed with the BLASTp or the tBLASTn program using default parameters to obtain either amino acid sequences (BLASTp) or nucleic acid sequences (tBLASTn) homologous to acyltransferase sequences of the invention. To obtain gapped alignments for comparison purposes, Gapped BLAST using default parameters can be utilized as described in Altschul et al. (Altschul 1997, Nucleic Acids Res. 25(17):3389-3402).

TABLE 1

Relation of sequence types of querry and hit sequences for various BLASt programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragment shall encode a polypeptide which still has desaturase and elongase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase or elongase activity to a significant extent, preferably, at least 10%, at least 20%, at least 30%, at least 40%, at least 50%, at least 60%, at least 70%, at least 80% or at least 90% of the desaturase and elongase activity exhibited by any of the polypeptide shown in any one of SEQ ID NOs: 2, 4, 6, 8 or 10. The activity may be tested as described in the accompanying Examples.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interefering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In the studies underlying the present invention, advantageously, polynucleotides where identified encoding desaturase and elongases from *Emilana huxleyi*. In particular, the *Emiliana huxleyi* desaturases Δ4Des(Eh), Δ8Des(Eh) and Δ5Des(Eh) and elongases Δ9Elo(Eh) and Δ5Elo(Eh) have been identified. Each of the desaturases are capable of introducing a double bond into fatty acids. For example, the expression of the Δ8Des(Eh) leads to introduction of a double bond at position eight into C20:2n-6 fatty acid. The polynucleotides of the present invention are particularly suitable for the recombinant manufacture of LCPUFAs and, in particular, ARA, EPA and/or DHA.

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, laclq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: lpt-2 or lpt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5

(Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alis, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the Ipt2 or Ipt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. N., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* sp.), sunflower (*Helianthus* sp.), cotton (*Gossypium* sp.), corn (*Zea mays*), olive (*Olea* sp.), safflower (*Carthamus* sp.), cocoa (*Theobroma* cocoa), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia* and *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LCPUFAs, i.e., the long chain unsaturated fatty acid biosynthetic pathway, are catalyzed by membrane-associated fatty acid desaturases and elongases. Plants and most other eukaryotic organisms have specialized desaturase and elongase systems for the introduction of double bonds and the extension of fatty acids beyond C18 atoms. The elongase reactions have several important features in common with the fatty acid synthase complex (FAS). However, the elongase complex is different from the FAS complex as the complex is localized in the cytosol and membrane bound, ACP is not involved and the elongase 3-keto-acyl-CoA-synthase catalyzes the condensation of malonyl-CoA with an acyl primer. The elongase complex consists of four components with different catalytic functions, the keto-acyl-synthase (condensation reaction of malonyl-CoA to acyl-CoA, creation of a 2 C atom longer keto-acyl-CoA fatty acid), the keto-acyl-reductase (reduction of the 3-keto group to a 3-hydroxy-group), the dehydratase (dehydration results in a 3-enoyl-acyl-CoA fatty acid) and the enoly-CoA-reductase (reduction of the double bond at position 3, release from the complex). For the production of LCPUFAs including ARA, EPA and/or DHA the elongation reactions, beside the desaturation reactions, are essential. Higher plants do not have the necessary enzyme set to produce LCPUFAs (4 or more double bonds, 20 or more C atoms). Therefore the catalytic activities have to be conferred to the plants or plant cells. The polynucleotides of the present invention catalyze the desaturation and elongation activities necessary for the formation of ARA, EPA and/or DHA. By delivering the novel desaturases and elongases increased levels of PUFAs and LCPUFAs are produced.

However, person skilled in the art knows that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: Δ-4-desaturase, Δ-5-desaturase, Δ-5-elongase, Δ-6-desaturase, 2-desaturase, 5-desaturase, ω3-desaturase and Δ-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-Desaturases d12Des (Co) from *Calendula officinalis* (WO200185968), d12Des (Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des (Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phy-* tophthora infestans (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from Ciona intestinalis (WO2005012316), d5Elo(OI) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(OI) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208). Particularly, if the manufacture of ARA is envisaged in higher plants, the enzymes recited in Table 3, below (i.e. additionally a d6-desaturase, d6-elongase, d5-elongase, d5-desaturase, d12-desaturase, and d6-elongase) or enzymes having essentially the same activity may be combined in a host cell. If the manufacture of EPA is envisaged in higher plants, the enzymes recited in Table 4, below (i.e. additionally a d6-desaturase, d6-elongase, d5-desaturase, d12-desaturase, d6-elongase, omega 3-desaturase and d15-desaturase), or enzymes having essentially the same activity may be combined in a host cell. If the manufacture of DHA is envisaged in higher plants, the enzymes recited in Table 5, below (i.e. additionally a d6-desaturase, d6-elongase, d5-desaturase, d12-desaturase, d6-elongase, omega 3-desaturase, d15-desaturase, d5-elongase, and d4-desaturase), or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising a) cultivating the host cell of the invention under conditions which allow for the production of the said polypeptide; and b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention also encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at abrf.org/index.cfm/dm.home). The polypeptides of the present invention shall exhibit the desaturase or elongase activity referred to above.

Encompassed by the present invention is, furthermore, an antibody or fragments thereof which specifically recognizes the polypeptide of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera Calendula, *Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrate, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculents* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon* columbiae, *Ceratodon* heterophyllus, *Ceratodon* purpureus, *Ceratodon* purpureus, *Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja* max [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon*

*drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense,* Geraniaceae, such as the genera *Pelargonium, Cocos, Oleum,* for example the genera and species *Cocos nucifera, Pelargonium grossularioides* or *Oleum cocois* [coconut], Gramineae, such as the genus *Saccharum,* for example the genus and species *Saccharum officinarum,* Juglandaceae, such as the genera *Juglans, Wallia,* for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus,* for example the genera and species *Laurus nobilis* [bay], *Persea americana, Persea gratissima* or *Persea persea* [avocado], Leguminosae, such as the genus *Arachis,* for example the genus and species *Arachis hypogaea* [peanut], Linaceae, such as the genera *Linum, Adenolinum,* for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica,* for example the genus and species *Punica granatum* [pomegranate], Malvaceae, such as the genus *Gossypium,* for example the genera and species *Gossypium hirsutum, Gossypium arboreum, Gossypium barbadense, Gossypium herbaceum* or *Gossypium thurberi* [cotton], Marchantiaceae, such as the genus *Marchantia,* for example the genera and species *Marchantia berteroana, Marchantia foliacea, Marchantia macropora,* Musaceae, such as the genus *Musa,* for example the genera and species *Musa nana, Musa acuminata, Musa paradisiaca, Musa* spp. [banana], Onagraceae, such as the genera *Camissonia, Oenothera,* for example the genera and species *Oenothera biennis* or *Camissonia brevipes* [evening primrose], Palmae, such as the genus *Elacis,* for example the genus and species *Elaeis guineensis* [oil palm], Papaveraceae, such as the genus *Papaver,* for example the genera and species *Papaver orientale, Papaver rhoeas, Papaver dubium* [poppy], Pedaliaceae, such as the genus *Sesamum,* for example the genus and species *Sesamum indicum* [sesame], Piperaceae, such as the genera *Piper, Artanthe, Peperomia, Steffensia,* for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum,* for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia,* for example the genus and species *Porphyridium cruentum,* Proteaceae, such as the genus *Macadamia,* for example the genus and species *Macadamia* intergrifolia [macadamia], Prasinophyceae such as the genera *Nephroselmis, Prasinococcus, Scherffelia, Tetraselmis, Mantoniella, Ostreococcus,* for example the genera and species *Nephroselmis olivacea, Prasinococcus capsulatus, Scherffelia dubia, Tetraselmis chui, Tetraselmis suecica, Mantoniella squamata, Ostreococcus tauri,* Rubiaceae such as the genus *Cofea,* for example the genera and species *Cofea* spp., *Coffea arabica, Coffea canephora* or *Coffea liberica* [coffee], Scrophulariaceae such as the genus *Verbascum,* for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon,* for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma,* for example the genus and species *Theobroma cacao* [cacao] or Theaceae, such as the genus *Camellia,* for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, Calendula, *Punica,* evening primrose, mullein, thistle, wild roses, hazelnut, almond, *macadamia,* avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, Calendula, *Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Emiliana, Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, lsochrysis galbana, Aleurita farinosa, Thraustochytrium sp., Muscarioides viallii, Mortierella alpine, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and Tables 3, 4 and 5).

Furthermore, the present invention encompasses a method for the manufacture of polyunsaturated fatty acids comprising:

a) cultivating the host cell of the invention under conditions which allow for the production of polyunsaturated fatty acids in said host cell;
b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4(8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the desaturase or elongase activity of the polypeptides of the present invention. Preferably, substrates encompass LA 18:2 (9,12), ALA 18:3(9,12,15), Eicosadienoic acid 20:2 (11,14), Eicosatrienoic acid 20:3 (11,14,17)), DGLA 20:3 (8,11,14), ARA 20:4 (5,8,11,14), eicosatetraenoic acid 20:4 (8,11,14, 17), Eicosapentaenoic acid 20:5 (5,8,11,14,17), Docosahexapentanoic acid 22:5 (7,10,13,16,19).

The term "cultivating" as used herein refers maintaining and growing the host cells under culture conditions which allow the cells to produce the said polyunsaturated fatty acid, i.e. the PUFA and/or LCPUFA referred to above. This implies that the polynucleotide of the present invention is expressed in the host cell so that the desaturase and/or elongase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in –CoA bound form, as membrane phospholipids or as triacylglyceride estres. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism.

Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batch-wise, semibatchwise or continuously. Nutrients can be provided at the beginning of the fermentation or administered semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:
a) cultivating the non-human transgenic organism of the invention under conditions which allow for the production of poly-unsaturated fatty acids in said non-human transgenic organism; and
b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GM P standard. Similar standards will apply for lipid or fatty acid compositions to be applied in cosmetic or pharmaceutical compositions. All these measures for formulating oil, lipid or fatty acid compositions as products are comprised by the aforementioned manufacture.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

The contents of all references cited throughout this application are herewith incorporated by reference in general and with respect to their specific disclosure content referred to above.

FIGURES

FIG. 1 shows a schematical figure of the different enzymatic activities leading to the production of ARA, EPA and DHA.

FIG. 2 shows a yeast expression experiment with feeding of 22:5n-3 in the prescence (A) and absence (B) of d4Des (Eh)

FIG. 3 shows a yeast expression experiment with feeding of 20:3n-3 in the prescence (A) and absence (B) of d8Des (Eh)

FIG. 4 shows a yeast expression experiment with feeding of 18:3n-3 in the prescence (A) and absence (B) of d9Elo (Eh)

FIG. 5 shows a yeast expression experiment with feeding of 18:3n-6 (GLA) and 18:4n-3 (SDA) in the prescence (A) and absence (B) of d5Elo(Eh)

FIG. 6 shows a yeast expression experiment with feeding of 20:4n-6 (ARA) and 20:5n-3 (EPA) in the prescence (A) and absence (B) of d5Elo(Eh)

FIG. 7 shows the expression of d9Elo(Eh) in seeds of two *Arabidopsis* events. As control seeds not expression d9Elo (Eh) are shown (WT).

FIG. 8 shows the Acyl-CoA analysis of mature *Arabidopsis* seeds from both events expressing the d9Elo(Eh) in comparison to seeds not expressing d9Elo(Eh) (Col0)).

FIG. 9 shows the expression of d9Elo(Eh), d8Des(Eh) and d5Des(Eh) in seeds of various *Arabidopsis* events.

FIG. 10 shows gas chromatographic analysis of mature *Arabidopsis* seeds transformed with the construct OstELO5EmD4. Peaks were quantified and listed in the table below. The products of d5Elo(Ot) and d4Des(Eh) activity are 22:6n-3 (DHA).

FIG. 11 is a comparison between two d4-desaturases (Tc and Eh) showing that d4Des(Eh) is different from known d4-desaturases in producing a high ratio of DHA:DPA.

FIG. 12 shows the expression of d5Elo(Eh) in seeds of various *Arabidopsis* events.

FIG. 13 is a comparison between three different d6-desaturases and the substrate specificity of d5Des(Eh).

This invention is further illustrated by the following examples which should not be construed as limiting. The contents of all references, patents and published patent applications cited throughout this application, as well as the figures, are incorporated herein by reference.

EXAMPLES

Example 1: Organism and Culture Conditions

*Emilana huxleyi* was grown as described in Sciandra et al. (2003) Marine Ecology Progress Series 261:111-122 with following conditions:

Growth in 50 ml inconical flasks using K/2 medium (Keller et al. (1987) Journal of Phycology 23:633-638). The flasks were placed in a growth chamber at a temperature of 17±0.1° C. under 14L:10D irradiance. Light was provided by fluorescent lamps giving a photon fluxdensity (400 to 700 nm) of 170 µmol photon m-2 s-1.

Example 2: Cloning of Novel Desaturase and Elongase Sequences

RNA from cells grown as described under Example 1 was extracted using the RNA-extraction Kit from Qiagen, a RACE-library was generated using the RACE-Kit from Clontech. From the RACE-library sequences for desaturase and elongases were amplified with PCR using following primer pairs and PCR conditions.

PCR reaction (50 µL):
5.00 µL Template cDNA
5.00 µL 10× Puffer (Advantage-Polymerase)+25 mM MgCl$_2$
5.00 µL 2 mM dNTP
1.25 µL je Primer (10 pmol/µL)
0.50 µL Advantage-Polymerase
The Advantage polymerase mix from Clontech was used.
Reaction conditions of the PCR:
Annealing: 1 min 55° C.
Denaturation: 1 min 94° C.
Elongation: 2 min 72° C.
Cycles: 35
Primer pairs used in PCR:

| Name | Primer pair (5' orientation) | SEQ ID NO. |
|---|---|---|
| Eh4ff | CCATGGGAGGCGCCGGCGCGAG | 11 |
| Eh4rv | CTAGTCCGCCTTGAGGTTCTC | 12 |
| Eh5ff | ACCATGTGCAAGGCGAGCGGCCT | 13 |
| Eh5rv | TCACCAATCATGAGGAAGGT | 14 |
| Eh8ff | CCATGGGCAAGGGCGGCAACGC | 15 |
| Eh8rv | GGGCAGAGATGCCGCACTAG | 16 |
| Eh9ff | ACCATGCTCGATCGCGCCTCGTC | 17 |
| Eh9rv | TCACAGCGCCTTGCGGGTAGC | 18 |

The PCR reactions resulted in following polynucleotide sequences:

| Gene | Activity | Length in bp | SEQ ID NO. |
|---|---|---|---|
| D4Des(Eh) | D4-desaturase | 1280 | 5 |
| D8Des(Eh) | D8-desaturase | 1256 | 1 |
| D9Elo(Eh) | D9-elongase | 804 | 3 |
| D5Elo(Eh) | Multi-elongase | 921 | 7 |

A list of identified full-length coding sequences is shown in Table 1.

TABLE 1

List of full-length coding sequences and deduced amino acid sequences

| SEQ ID NO: | Gene | Coding sequence in bp | Amino acid sequence |
|---|---|---|---|
| 1 | D8Des(Eh) | 1254 | 417 |
| 3 | D9Elo(Eh) | 801 | 266 |
| 5 | D4Des(Eh) | 1278 | 425 |
| 7 | D5Elo(Eh) | 918 | 305 |

Open reading frames as shown in Table 1 were cloned into the pESC(Leu) vector from Stratagene according to manufactures reaction conditions. Reactions were transformed into *E. coli* DH5α and plasmid DNA was isolated. The plasmids pESC-d4Des(Eh), pESC-d8Des(Eh), pESC-d9Elo(Eh), pESC-d5Elo(Eh) were then used for yeast transformation.

Example 3: Yeast Transformation and Growth Conditions

*S. cerevisiae* strain INVSC from Invitrogen was transformed with the constructs pESC-d4Des(Eh), pESC-d8Des(Eh), pESC-d9Elo(Eh), pESC-d5Elo(Eh) and pESC using the S. C. EasyComp Transformation Kit (Invitrogen, Carlsbad, Calif.) with selection on leucine-deficient medium.

Yeast were grown after transformation in complete medium containing all amino acids and nucleotides. Then yeast were plated on different medium containing either the complete medium (SD) or the complete medium lacking leucine (SD-Leu). Only yeast containing pESC-d4Des(Eh), pESC-d8Des(Eh), pESC-d9Elo(Eh), pESC-d5Elo(Eh) or pESC vector can grow on this medium.

Example 4: Functional Expression of Desaturases and Elongases in Yeast and Gas Chromatographic Analysis Yeast cells containing the respective pESC plasmids as prepared above were incubated 12 h in liquid DOB-U medium at 28° C., 200 rpm inkubiert and than additional 12 h in induction medium (DOB-U+2% (w/v) galactose+2% (w/v) raffinose). To the induction medium 250 µM of the respective fatty acids were added to check for enzyme activity and specificity.

Yeast cells were analyzed as following:

Yeast cells from induction medium were harvested by centrifugation (100×g, 5 min, 20° C.) and washed with 100 mM NaHCO$_3$, pH 8.0, to remove residual fatty acids. From the yeast pellet a total extract of fatty acid methylesters (FAME) was generated by adding 2 ml 1 N methanolic sulfuric acid and 2% (v/v) Dimethoxypropan for 1 h at 80° C. FAME were extracted two times with Petrolether (PE). Not derivased fatty acids were removed by washing with 2 ml 100 mM NaHCO$_3$, pH 8.0 and 2 ml Aqua dest. The PE-phases were dried with Na$_2$SO$_4$ and eluted in 100 µl PE. The samples were then separated with a DB-23-column (30 m, 0.25 mm, 0.25 µm, Agilent) in a Hewlett-Packard 6850-machine with FID using following conditions: oven temperature 50° C. to 250° C. with a rate of 5° C./min and finally 10 min at 250° C.

The identification of the fatty acids was done using the retention times of known fatty acid standards (Sigma). The method is described e.g. in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 5: Functional Characterization of d4Des(Eh)

As described above d4Des(Eh) was functionally characterized in yeast. The result of the analysis is shown in FIG. 2. Yeast transformed with pESC-d4Des(Eh) was compared to yeast transformed with pESC (control) while feeding the yeast cells with the fatty acid DPA 22:5n-3. Based on this comparison pESC-d4Des(Eh) exhibits d4-desaturase activity as in the control no 22:6 is observed. Therefore d4Des(Eh) is a functional d4-desaturase.

Example 6: Functional Characterization of d8Des(Eh)

As described above d8Des(Eh) was functionally characterized in yeast. The result of the analysis is shown in FIG. 3. Yeast transformed with pESC-d8Des(Eh) was compared to yeast transformed with pESC (control) while feeding the fatty acid 20:3n-3. Based on this comparison a new fatty acid was formed compared to the control, which is 20:4n-3. The formation of this fatty acid proves that d8Des(Eh) was functionally expressed and has d8-desaturase activity. The conversion rate of 20:3n-3 to 20:4n-3 was 5%.

Example 7: Functional Characterization of d9Elo(Eh)

As described above d9Elo(Eh) was functionally characterized in yeast. The result of the analysis is shown in FIG. 4. Yeast transformed with pESC-d9Elo(Eh) was compared to yeast transformed with pESC (control) while feeding the fatty acids 18:3n-3 (ALA) or 18:2 (LA). Based on this comparison a new fatty acid was formed compared to the control, which is 20:3n-3 or 20:2n-6, respectively. The formation of these fatty acids proves that d9Elo(Eh) was functionally expressed and has d9-elongase activity. The conversion rate of 18:3n-3 to 20:3n-3 was 17%, the conversion rate of 18:2n-6 to 20:2n-6 was 49%.

Example 8: Functional Characterization of d5Elo(Eh)

As described above d5Elo(Eh) was functionally characterized in yeast. The result of the analysis is shown in FIGS. 5 and 6. Yeast transformed with pESC-d5Elo(Eh) was compared to yeast transformed with pESC (control) while feeding the fatty acids 18:3n-6 (GLA), 18:4 (SDA) or 20:4n-6 (ARA), 20:5n-3 (EPA), respectively. Based on this comparison new fatty acids formation was observed when compared to the control, which is 20:3n-6 or 20:4n-3 when fed GLA or SDA and 22:4n-6 or 22:5n-3 when fed ARA or EPA, respectively. The formation of these fatty acids proves that d5Elo(Eh) was functionally expressed and has d5-elongase activity. The conversion rate of GLA was 13%, the conversion rate of 18:4n-3 was 30%, the conversion rate of ARA was 38% and the conversion rate of EPA was 30%. Surprisingly the elongase used a wide variety of substrates of elongation. The specification indicates a multifunctional elongase activity with higher specificities for omega3 fatty acids.

Example 9: Expression of Novel Elongases from *Emilana huxleyi* in Plants

The novel desaturases and elongases were cloned into a plant transformation vector as described in WO2003/093482, WO2005/083093 or WO2007/093776. Exemplary suitable combinations of genes are described in Table 2, 3 and 4.

TABLE 2

Gene combinations for the production of ARA.

| Gene | Activity | SEQ ID NO: |
|---|---|---|
| D6Des(Ot) | Δ6-Desaturase | 19 |
| D6Elo(Pp) | Δ6-Elongase | 21 |
| D5Des(Eh) | Δ5-Desaturase | 9 |
| D12Des(Ps) | Δ12-Desaturase | 23 |
| D6Elo(Tp) | Δ6-Elongase | 25 |
| D8Des(Eh) | Δ8-Desaturase | 1 |
| D9Elo(Eh) | Δ9-Elongase | 3 |

TABLE 3

Gene combinations for the production of EPA.

| Gene | Activity | SEQ ID NO: |
|---|---|---|
| D6Des(Ot) | Δ6-Desaturase | 19 |
| D5Elo(Eh) | Δ5-Elongase | 7 |
| D5Des(Eh) | Δ5-Desaturase | 9 |
| D12Des(Ps) | Δ12-Desaturase | 23 |
| D6Elo(Tp) | Δ6-Elongase | 25 |
| o3-Des(Pi) | Omega 3-Desaturase | 27 |
| D15Des(Cp) | Δ15-Desaturase | 29 |
| D8Des(Eh) | Δ8-Desaturase | 1 |
| D9Elo(Eh) | Δ9-Elongase | 3 |

TABLE 4

Gene combinations for the production of DHA.

| Gene | Activity | SEQ ID NO: |
|---|---|---|
| D6Des(Ot) | Δ6-Desaturase | 19 |
| D5Elo(Eh) | Δ5-Elongase | 7 |
| D5Des(Eh) | Δ5-Desaturase | 9 |
| D12Des(Ps) | Δ12-Desaturase | 23 |
| D6Elo(Tp) | Δ6-Elongase | 25 |
| ω3-Des(Pi) | Omega 3-Desaturase | 27 |
| D15Des(Cp) | Δ15-Desaturase | 29 |
| D5Elo(Ot) | Δ5-elongase | 31 |
| D4Des(Eh) | Δ4-desaturase | 5 |

TABLE 4-continued

Gene combinations for the production of DHA.

| Gene | Activity | SEQ ID NO: |
|---|---|---|
| D8Des(Eh) | Δ8-Desaturase | 1 |
| D9Elo(Eh) | Δ9-Elongase | 3 |

Based on the gene combinations as described in Table 2, Table 3 or Table 4 following combinations were designed
AP2: LuCnI-d5Des(Eh)_LuCnI-d8Des8Eh)_Napin-o3Des(PO_Napin-d12Des(Ps)_LuCnI-d9Elo(Eh)
OstELO5EmD4: VfUSP-d6Elo(Pp)_LuCnI-d5Des8Tc)_VfSBP-d6Des(Ot)_Napin-o3Des(PO_Napin-d12Des(Ps)_LuCnI-d5Elo(Ot)_LuCnI-d4Des(Eh)
OstELO5TcD4: VfUSP-d6Elo(Pp)_LuCnI-d5Des8Tc)_VfSBP-d6Des(Ot)_Napin-o3Des(PO_Napin-d12Des(Ps)_LuCnI-d5Elo(Ot)_LuCnI-d4Des(Tc)

Transgenic rapeseed lines were generated as described in Deblaere et al, 1984, Nucl. Acids. Res. 13, 4777-4788 and seeds of transgenic rapeseed plants are analyzed as described in Qiu et al. 2001, J. Biol. Chem. 276, 31561-31566.

Transgenic *Arabidopsis* plants were generated as described in Bechtholdt et al. 1993 *C. R. Acad. Sci. Ser. III Sci. Vie.*, 316, 1194-1199. Seeds of transgenic *Arabidopsis* plants expressing d9Elo(Eh) by using the seed-specific promoter Glycinin from soybean (Lelievre et al. (1992) Plant Physiol 98:387-391) were analyzed by gas chromatography (FIG. 7). Compared to non-transgenic control plants (WT) there are changes in the fatty acid profile, proving that d9Elo(Eh) was functionally expression in seeds. The major shifts in the fatty acid profile is directed to a 10fold increase in the fatty acid 20:2n-6 and 20:3n-3 (FIG. 7). Therefore d9Elo(Eh) exhibits a Δ9-elongase activity, which is consistent with the yeast characterization. Further, the levels of 18:2 and ALA in the transgenic events expressing d9Elo(Eh) are lowered compared to WT, as these fatty acids are direct substrates for the d9Elo(Eh). Further, the endogenous elongation system in the plant is unchanged as levels of 20:1 and 22:1 are similar between transgenic plants expression d9Elo(Eh) and WT control. This indicates that the expression of d9Elo(Eh) does not disturb endogenous elongation process, but delivers additional activity.

To further prove the activity of d9Elo(Eh) expressed in seeds of *Arabidopsis thaliana* AcylCoA-measurements were done. Substrates and products of the d9Elo(Eh) elongation reaction are AcylCoA-esters, which are then further incorporated into triacylglycerides (oil). The analysis of the acylCoA-pool reveals the formation and flux of the elongation reaction.

FIG. 8 summarizes the AcylCoA measurements for *Arabidopsis* event expressing d9Elo(Eh) in comparison to controls not expressing d9Elo(Eh) (Col0). The change in the chromatogram is indicated by a star. At this position a massive amount of 20:2n-6 is detected, which is much lower in the control. The conditions for separation of the fatty acid CoA-esters does not allow the detection of 20:3n-3 as this CoA ester is not separated from 18:3CoA.

The massive occurrence of 20:2n-6-CoA proves the expression of d9Elo(Eh) as this is the direct product of its enzymatic activity.

Further, transgenic *Arabidopsis* lines have been generated to validate the activity of d8Des(Eh) and d5Des(Eh). Vector AP2 has been constructed according to standard molecular biology steps as described in WO2003/093482, WO2005/083093, WO2007/093776 or WO2009/016202 and transformed into *Arabidopsis thaliana* as described above. Analysis of transgenic seeds is shown in FIG. 9. The products of d9Elo(Eh) are 20:2 and 20:3n-3.

Further, transgenic *Arabidopsis* lines have been generated to validate the activity of d4Des(Eh). Construct OstELO5EmD4 was transformed into *Arabidopsis* as described above and seeds of a number of individual lines have been analyzed by gas chromatography (FIG. 10). The activity of d4Des(Eh) is demonstrated by the formation of DHA 22:6 (last column). All lines show the production of DHA with levels of up to 4.7%. Of special interest is the ratio of DHA to DPA. Surprisingly the ratio of d4Des(Eh) is much higher than in d4-desaturases known in the art. A comparison against the d4-desaturase from *Thraustochytrium* ssp. of WO2002/026946 is shown in FIG. 11. The enzyme from *Thraustochytrium* ssp. showed so far highest levels of DHA (WO2005/083093), but with an unfavorable ratio of DPA to DHA. A high ratio of DHA:DPA is for the commercial use of such oils of importance.

Further, transgenic *Arabidopsis* lines have been generated to validate the activity of d5Elo(Eh). Construct EmELO5TcD4 was transformed into *Arabidopsis* as described above and seeds of a number of individual lines have been analyzed by gas chromatography (FIG. 12). The activity of d5Elo(Eh) is demonstrated by the formation of DPA 22:5 and DHA 22:6. Most lines show the production of these two fatty acids, proofing that d5Elo(Em) is functionally expressed in the seeds.

Further, transgenic *Arabidopsis* lines have been generated to validate the activity and substrate specificity of d5Des (Eh). For this purpose two Δ6-desaturases were selected based on their different substrate specificity. The borageΔ6 is expected to use phosphatidylcholin-18:2 as substrate (WO96/21022), whereas the *Ostreococcus* Δ6 (OstrΔ6) uses Acyl-CoA ester (WO2005/012316). In combination with the d6-elongase from *Physcomllrella patens* (WO2001/059128) both d6-desaturases produce DGLA or 20:4n-3, respectively. The ratio of ARA to EPA is for the borageΔ6 2.9, for the OstrΔ6 2.3. It is noted that the use of OstrΔ6 results in 3-4 times higher levels of products compared to the borageΔ6. The further combination of the d5Des(Eh) resulted in the production of ARA and EPA, demonstrating the functionality of the d5Des(Eh). The conversion of d5Des (Eh) of DGLA to ARA is 29% (borageΔ6) or 47% (OstrΔ6). For 20:4n-3 to EPA it is 33% (borageΔ6) or 26% (OstrΔ6).

Based on these results it is concluded that for Acyl-CoA substrates d5Des(Eh) is specific for the omega6 fatty acid DGLA. This is a novel substrate specificity not observed in the state of the art d5-desaturases.

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella* alpine by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbiol. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant Microbe Interact. 15, 303-312.

Okuley, J., Lightner, J., Feldmann, K., Yadav, N., Lark, E., and Browse, J. (1994). *Arabidopsis* FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Qiu, X., Hong, H., and McKenzie, S L. (2001) Identification of a Delta 4 fatty acid desaturase from *Thraustochytrium* sp. involved in the biosynthesis of docosahexanoic acid by heterologous expression in *Saccharomyces cerevisiae* and *Brassica juncea*. J Biol Chem 276, 31561-6.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Tudzynski, P., Correia, T., and Keller, U. (2001). Biotechnology and genetics of ergot alkaloids. Appl. Microbiol. Biotechnol. 57, 593-605.

All references cited in this specification are herewith incorporated by reference with respect to their entire disclosure content and the disclosure content specifically mentioned in this specification.

We claim:

1. Plant seed oil obtained from seeds of a transgenic plant, wherein the oil comprises at least 1% docosahexaenoic acid (DHA) and at least 1% but not more than 6% eicosapentaenoic acid (EPA), based on the total fatty acids of the transgenic seeds, and wherein the oil has a ratio of DHA to docosapentaenoic acid (DPA) of at least 2.

2. The oil of claim 1, wherein the transgenic plant is a transgenic oilseed plant.

3. The oil of claim 2, wherein the oilseed plant is flax (Linum sp.), rapeseed (Brassica sp.), soybean (Glycine sp.), sunflower (Helianthus sp.), cotton (Gossypium sp.), corn (Zea mays), olive (Olea sp.), safflower (Carthamus sp.), cocoa (Theobroma cacoa), peanut (Arachis sp.), hemp, camelina, crambe, oil palm, coconuts, groundnuts, sesame, castor bean, lesquerella, tallow tree, sheanuts, tungnuts, kapok fruit, poppy, jojoba, or perilla.

4. The oil of claim 2, wherein the oilseed plant is from the plant family of Brassicaceae.

5. The oil of claim 2, wherein the oilseed plant is a Brassica plant.

6. The oil of claim 1, wherein the oil has a ratio of DHA to DPA of 2.9.

7. The oil of claim 1, wherein the oil comprises at least 1% but not more than 5% EPA.

8. The oil of claim 1, wherein the DHA, EPA and DPA are triglyceride esters.

9. Plant seed oil obtained from seeds of a transgenic plant, wherein the oil comprises at least 1% docosahexaenoic acid (DHA) and at least 1% but not more than 6% eicosapentaenoic acid (EPA), based on the total fatty acids of the transgenic seed, and wherein the seeds of the transgenic plant have a conversion rate of docosapentaenoic acid (DPA) to DHA of at least 75%.

10. The oil of claim 9, wherein the transgenic plant is a transgenic oilseed plant.

11. The oil of claim 10, wherein the oilseed plant is flax (Linum sp.), rapeseed (Brassica sp.), soybean (Glycine sp.), sunflower (Helianthus sp.), cotton (Gossypium sp.), corn (Zea mays), olive (Olea sp.), safflower (Carthamus sp.), cocoa (Theobroma cacoa), peanut (Arachis sp.), hemp, camelina, crambe, oil palm, coconuts, groundnuts, sesame, castor bean, lesquerella, tallow tree, sheanuts, tungnuts, kapok fruit, poppy, jojoba, or perilla.

12. The oil of claim 10, wherein the oilseed plant is from the plant family of Brassicaceae.

13. The oil of claim 10, wherein the oilseed plant is a Brassica plant.

14. The oil of claim 9, wherein the oil has a ratio of DHA to DPA of at least 2.

15. The oil of claim 14, wherein the ratio of DHA to DPA is 2.9.

16. The oil of claim 9, wherein the oil comprises at least 1% but not more than 5% EPA.

17. The oil of claim 9, wherein the DHA, EPA and DPA are triglyceride esters.

* * * * *

(12) POST-GRANT REVIEW CERTIFICATE (221st)

United States Patent
Bauer et al.

(10) Number: US 10,351,870 J1
(45) Certificate Issued: Feb. 11, 2022

(54) USES OF NOVEL FATTY ACID DESATURASES AND ELONGASES AND PRODUCTS THEREOF

(71) Applicants: Jörg Bauer; Jonathan A. Napier; Olga Sayanova

(72) Inventors: Jörg Bauer; Jonathan A. Napier; Olga Sayanova

(73) Assignee: BASF PLANT SCIENCE COMPANY GMBH

Trial Number:

PGR2020-00057 filed Apr. 16, 2020

Post-Grant Review Certificate for:

Patent No.: 10,351,870
Issued: Jul. 16, 2019
Appl. No.: 15/351,962
Filed: Nov. 15, 2016

The results of PGR2020-00057 are reflected in this post-grant review certificate under 35 U.S.C. 328(b).

POST-GRANT REVIEW CERTIFICATE
U.S. Patent 10,351,870 J1
Trial No. PGR2020-00057
Certificate Issued Feb. 11, 2022

AS A RESULT OF THE POST-GRANT REVIEW PROCEEDING, IT HAS BEEN DETERMINED THAT:

Claims 1-17 are cancelled.

\* \* \* \* \*

SEQUENCE LISTING

```
<160> NUMBER OF SEQ ID NOS: 32

<210> SEQ ID NO 1
<211> LENGTH: 1256
<212> TYPE: DNA
<213> ORGANISM: Emiliana huxleyi

<400> SEQUENCE: 1
ccatgggcaa gggcggcaac gcgaacccgc gggagctcaa aggcggcaag gccgagcagc      60
tgacagtcta cctgtatggc aaggctgtcg acgtctcgaa gttcgcgaag ctgcacccgg     120
gaggcgccaa ggcgctgcgc atcttcaaca accgcgacgc caccgagcag ttcgagatgt     180
accactcgcc cgccgcccac aagatgatgc gtgcgatgtc gaagagcgcg ccggaggccc     240
cgagggagag cgaggtcgcg acgtcggtcg ttgggacgga cttcgccaag ctgacgcaga     300
cgctgcacga cgtcggatgc ttcgacccgc actaccctga cgaggccttc aagctcggcc     360
tcacgctgct gcccggattc ctcggcttct acctgctgcg gagcggcatg ccggcgctcg     420
gatccttcct gatcgctttc tcgtactaca tgtcggggtg gacctcccac gattacttgc     480
accacggctg cctcaagggc ggccaaaagc agctggtgca ctggaacaac gccgtcggct     540
acgcaatcgg cgcttggcag ggctacgcgg tcggctggtg gcgagcgcgc cacaacacgc     600
accacctcgt cactaacgaa gaaggcaacg accccgacat catgaccgcg cccgtgctca     660
tcttcgtgcg caacagcccg gtgatcgccg ctgccctcaa cgcggcgcag cggtggcagc     720
agtactacta cgtgcccgcg atgagcctca tggacatgta ctggcgcttc gagtcgatgc     780
agtacctggc cgcgcgaccc ttcaacaagg tgtgggcctc gtgggcgctc ctcgcgctgc     840
actactcctt tgtcggctac atgttccacg gacagtacca gtggctgctg ctgacgatgc     900
tggtgcgcgg cttcctcacg ggcatcgtcg tcttctcgac gcattatggc gaggaggtca     960
tcccgggcga ccacggcatg acactcgtcg agcagacggc gctcacctct cgcaacatca    1020
ccggcgggta cctcgtcaac ctgctcacgg gctacatctc gctgcagacg gagcaccacc    1080
tctggccgat gatgcccacc gcgcgcctcg aggcggcga gccctacgcg cgcgccttct    1140
tcaagaagca cggcttcgtc taccgcgagt cgaacctcgt cgagtgcgtc aagtacaaca    1200
tcgccgccct cgacatccgc acgcgcaacg gcgagtgggc agagatgccg cactag        1256
```

```
<210> SEQ ID NO 2
<211> LENGTH: 417
<212> TYPE: PRT
<213> ORGANISM: Emiliana huxleyi

<400> SEQUENCE: 2

Met Gly Lys Gly Gly Asn Ala Asn Pro Arg Glu Leu Lys Gly Gly Lys
1               5                   10                  15

Ala Glu Gln Leu Thr Val Tyr Leu Tyr Gly Lys Ala Val Asp Val Ser
            20                  25                  30

Lys Phe Ala Lys Leu His Pro Gly Gly Ala Lys Ala Leu Arg Ile Phe
        35                  40                  45

Asn Asn Arg Asp Ala Thr Glu Gln Phe Glu Met Tyr His Ser Pro Ala
    50                  55                  60

Ala His Lys Met Met Arg Ala Met Ser Lys Ser Ala Pro Glu Ala Pro
65                  70                  75                  80

Arg Glu Ser Glu Val Ala Thr Ser Val Val Gly Thr Asp Phe Ala Lys
                85                  90                  95

Leu Thr Gln Thr Leu His Asp Val Gly Cys Phe Asp Pro His Tyr Pro
            100                 105                 110

Asp Glu Ala Phe Lys Leu Gly Leu Thr Leu Leu Pro Gly Phe Leu Gly
        115                 120                 125

Phe Tyr Leu Leu Arg Ser Gly Met Pro Ala Leu Gly Ser Phe Leu Ile
    130                 135                 140

Ala Phe Ser Tyr Tyr Met Ser Gly Trp Thr Ser His Asp Tyr Leu His
145                 150                 155                 160

His Gly Cys Leu Lys Gly Gly Gln Lys Gln Leu Val His Trp Asn Asn
                165                 170                 175

Ala Val Gly Tyr Ala Ile Gly Ala Trp Gln Gly Tyr Ala Val Gly Trp
            180                 185                 190

Trp Arg Ala Arg His Asn Thr His His Leu Val Thr Asn Glu Glu Gly
        195                 200                 205

Asn Asp Pro Asp Ile Met Thr Ala Pro Val Leu Ile Phe Val Arg Asn
    210                 215                 220

Ser Pro Val Ile Ala Ala Leu Asn Ala Ala Gln Arg Trp Gln Gln
225                 230                 235                 240

Tyr Tyr Tyr Val Pro Ala Met Ser Leu Met Asp Met Tyr Trp Arg Phe
                245                 250                 255

Glu Ser Met Gln Tyr Leu Ala Ala Arg Pro Phe Asn Lys Val Trp Ala
            260                 265                 270

Ser Trp Ala Leu Leu Ala Leu His Tyr Ser Phe Val Gly Tyr Met Phe
        275                 280                 285

His Gly Gln Tyr Gln Trp Leu Leu Leu Thr Met Leu Val Arg Gly Phe
    290                 295                 300

Leu Thr Gly Ile Val Val Phe Ser Thr His Tyr Gly Glu Glu Val Ile
305                 310                 315                 320

Pro Gly Asp His Gly Met Thr Leu Val Glu Gln Thr Ala Leu Thr Ser
                325                 330                 335

Arg Asn Ile Thr Gly Gly Tyr Leu Val Asn Leu Leu Thr Gly Tyr Ile
            340                 345                 350

Ser Leu Gln Thr Glu His His Leu Trp Pro Met Met Pro Thr Ala Arg
        355                 360                 365

Leu Glu Ala Ala Gln Pro Tyr Ala Arg Ala Phe Phe Lys Lys His Gly
    370                 375                 380
```

Phe Val Tyr Arg Glu Ser Asn Leu Val Glu Cys Val Lys Tyr Asn Ile
385                 390                 395                 400

Ala Ala Leu Asp Ile Arg Thr Arg Asn Gly Glu Trp Ala Glu Met Pro
            405                 410                 415

His

<210> SEQ ID NO 3
<211> LENGTH: 804
<212> TYPE: DNA
<213> ORGANISM: Emiliana huxleyi

<400> SEQUENCE: 3
accatgctcg atcgcgcctc gtccgacgcg gccatctggt ctgcggtgtc cgatccggaa      60
atcctgatcg gcactttctc ctacctgctg ctcaagccgc tgctacgcaa ctcagggctc     120
gtggacgagc ggaaaggcgc ctaccggacc tcgatgatct ggtacaacgt ggtgctcgcg     180
ctcttctccg cgacgagctt ctacgtgact gcgaccgcgc tcgggtggga caagggcacc     240
ggcgagtggc tccgcagtct cacgggcgac agcccgcagc agctgtggca atgcccgtcg     300
agggtatggg actccaagct gttcctgtgg acggccaagg ccttctacta ctcaaagtac     360
gtggagtacc tcgacacggc gtggctcgtc ctcaagggga agaaggtctc cttcctgcag     420
ggcttccacc actttggcgc gccgtgggac gtgtacctgg cattcggct gaagaacgag      480 ggcgtgtgga tcttcatgtt cttcaactcg ttcatccaca cggtcatgta cacgtactac     540
ggcctcaccg ccgcgggcta caagatccgc ggcaagccga tcatcaccgc gatgcaaata     600
agccagttcg tcgtcggctt tgtcctagtg tgggactaca tcaacgtgcc gtgcttccac     660
gccgacgccg ggcaggtctt cagctgggtc tttaactatg cttacgtcgg ctccgtcttt     720
ctgctctttt gccacttctt ctacatggac aacatcgcga aggccaaggc caagaaggcc     780
gtcgctaccc gcaaggcgct gtga                                            804

<210> SEQ ID NO 4
<211> LENGTH: 266
<212> TYPE: PRT
<213> ORGANISM: Emiliana huxleyi

<400> SEQUENCE: 4

Met Leu Asp Arg Ala Ser Ser Asp Ala Ala Ile Trp Ser Ala Val Ser
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Arg Lys Gly Ala Tyr Arg
        35                  40                  45

Thr Ser Met Ile Trp Tyr Asn Val Val Leu Ala Leu Phe Ser Ala Thr
    50                  55                  60

Ser Phe Tyr Val Thr Ala Thr Ala Leu Gly Trp Asp Lys Gly Thr Gly
65                  70                  75                  80

Glu Trp Leu Arg Ser Leu Thr Gly Asp Ser Pro Gln Gln Leu Trp Gln
                85                  90                  95

Cys Pro Ser Arg Val Trp Asp Ser Lys Leu Phe Leu Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Lys Val Ser Phe Leu Gln Gly Phe His His Phe
    130                 135                 140

Gly Ala Pro Trp Asp Val Tyr Leu Gly Ile Arg Leu Lys Asn Glu Gly
145                 150                 155                 160

Val Trp Ile Phe Met Phe Phe Asn Ser Phe Ile His Thr Val Met Tyr
                165                 170                 175

Thr Tyr Tyr Gly Leu Thr Ala Ala Gly Tyr Lys Ile Arg Gly Lys Pro
            180                 185                 190

Ile Ile Thr Ala Met Gln Ile Ser Gln Phe Val Gly Gly Phe Val Leu
        195                 200                 205

Val Trp Asp Tyr Ile Asn Val Pro Cys Phe His Ala Asp Ala Gly Gln
    210                 215                 220

Val Phe Ser Trp Val Phe Asn Tyr Ala Tyr Val Gly Ser Val Phe Leu
225                 230                 235                 240

Leu Phe Cys His Phe Phe Tyr Met Asp Asn Ile Ala Lys Ala Lys Ala
                245                 250                 255

Lys Lys Ala Val Ala Thr Arg Lys Ala Leu
            260                 265

<210> SEQ ID NO 5
<211> LENGTH: 1280
<212> TYPE: DNA
<213> ORGANISM: Emiliana huxleyi

<400> SEQUENCE: 5
ccatgggagg cgccggcgcg agcgaggctg aacggcccaa gtggaccacg atccacgggc      60
ggcacgtcga tgtgtcaaag ttccgccacc cgggtgggaa catcatcgag ctcttctatg     120
gcatggactc gacgagcgcg ttcgagcagt tccacggcca ccacaagggc gcgtggaaga     180
tgctcaaggc gctgccgacc aaggaggtcg accccgccga cgtgccgcag cagccgcagg     240
agcacgttgc cgagatgacg cggctgatga cgtcgtggcg cgagcgcggc ctctttaagc     300
cgcgccccgt cgcctcgggc atctacggtc tcgccgtcgt cgctgccatc gtcgcgtgca     360
tcgcctgcgc gccgcacgcg ccggtgctga gcgggatcgg gctcggcagc tgctgggcgc     420
agtgcggctt cctgcagcac atgggcgggc accgcgagtg ggggtgcgg tactccttcc     480
tcctgcagca cttcttcgag ggcctcctca agggcgggtc cgcctcgtgg tggcgcaacc     540
gccacaacaa gcatcacgca agactaacg tgctcggcga ggacggcgac ctgcggacga     600
ctcccttctt cgcctgggac ccgacgctcg ccaagaaggt tccagactgg tcgctcaaga     660
cgcaggcctt caccttcctc cccgccctcg gagcgtacgt cttgtcttt gccttcacga     720
tccgcaagta tgccgtcgtc aagaagctct ggcacgagct cgcactcatg atcgcgcact     780
acgcgatgtt ctactacgcg ctgcagctcg ccggtgcgtc gctcggcagc ggcctcgcct     840
tttactgcac cggctacgcc tggcaaggca tctacctcgg cttcttcttc ggcctgtccc     900
acttcgcggt cgagcgagtc ccctccaccg ccacctggct cgagtcgtcc atgatcggca     960
ccgtcgactg gggaggctcc tccgcctttt gcggctacgt ctccggcttc ctcaacatcc    1020
agatcgagca ccacatggcg ccgcagatgc cgatggagaa cctgcgccag atccgcgccg    1080
actgcaaggc gagcgcggag aagctcgggc ttccctatcg cgagctctcc ttcgccggcg    1140
cggtcaagct gatgatggtc ggcctctggc gcaggggag ggacgagctg cagctgcgct    1200
ccgacaggcg caagtactcg cgcacccagg cctacatggc ggccgcctcg gcggtggtgg    1260
agaacctcaa ggcggactag                                                1280

<210> SEQ ID NO 6
<211> LENGTH: 425
<212> TYPE: PRT
<213> ORGANISM: Emiliana huxleyi

<400> SEQUENCE: 6

Met Gly Gly Ala Gly Ala Ser Glu Ala Glu Arg Pro Lys Trp Thr Thr
1               5                   10                  15

Ile His Gly Arg His Val Asp Val Ser Lys Phe Arg His Pro Gly Gly
            20                  25                  30

Asn Ile Ile Glu Leu Phe Tyr Gly Met Asp Ser Thr Ser Ala Phe Glu
        35                  40                  45

Gln Phe His Gly His His Lys Gly Ala Trp Lys Met Leu Lys Ala Leu
    50                  55                  60

Pro Thr Lys Glu Val Asp Pro Ala Asp Val Pro Gln Gln Pro Gln Glu
65                  70                  75                  80

His Val Ala Glu Met Thr Arg Leu Met Thr Ser Trp Arg Glu Arg Gly
                85                  90                  95

Leu Phe Lys Pro Arg Pro Val Ala Ser Gly Ile Tyr Gly Leu Ala Val
            100                 105                 110

Val Ala Ala Ile Val Ala Cys Ile Ala Cys Ala Pro His Ala Pro Val
        115                 120                 125

Leu Ser Gly Ile Gly Leu Gly Ser Cys Trp Ala Gln Cys Gly Phe Leu
    130                 135                 140

Gln His Met Gly Gly His Arg Glu Trp Gly Val Arg Tyr Ser Phe Leu
145                 150                 155                 160

Leu Gln His Phe Phe Glu Gly Leu Leu Lys Gly Ser Ala Ser Trp
                165                 170                 175

Trp Arg Asn Arg His Asn Lys His His Ala Lys Thr Asn Val Leu Gly
            180                 185                 190

Glu Asp Gly Asp Leu Arg Thr Thr Pro Phe Phe Ala Trp Asp Pro Thr
        195                 200                 205

Leu Ala Lys Lys Val Pro Asp Trp Ser Leu Lys Thr Gln Ala Phe Thr
    210                 215                 220

Phe Leu Pro Ala Leu Gly Ala Tyr Val Phe Val Phe Ala Phe Thr Ile
225                 230                 235                 240

Arg Lys Tyr Ala Val Val Lys Lys Leu Trp His Glu Leu Ala Leu Met
                245                 250                 255

Ile Ala His Tyr Ala Met Phe Tyr Tyr Ala Leu Gln Leu Ala Gly Ala
            260                 265                 270

Ser Leu Gly Ser Gly Leu Ala Phe Tyr Cys Thr Gly Tyr Ala Trp Gln
        275                 280                 285

Gly Ile Tyr Leu Gly Phe Phe Phe Gly Leu Ser His Phe Ala Val Glu
    290                 295                 300

Arg Val Pro Ser Thr Ala Thr Trp Leu Glu Ser Ser Met Ile Gly Thr
305                 310                 315                 320

Val Asp Trp Gly Gly Ser Ser Ala Phe Cys Gly Tyr Val Ser Gly Phe
                325                 330                 335

Leu Asn Ile Gln Ile Glu His Met Ala Pro Gln Met Pro Met Glu
            340                 345                 350

Asn Leu Arg Gln Ile Arg Ala Asp Cys Lys Ala Ser Ala Glu Lys Leu
        355                 360                 365

Gly Leu Pro Tyr Arg Glu Leu Ser Phe Ala Gly Ala Val Lys Leu Met
    370                 375                 380

```
Met Val Gly Leu Trp Arg Thr Gly Arg Asp Glu Leu Gln Leu Arg Ser
385                 390                 395                 400

Asp Arg Arg Lys Tyr Ser Arg Thr Gln Ala Tyr Met Ala Ala Ala Ser
            405                 410                 415

Ala Val Val Glu Asn Leu Lys Ala Asp
        420                 425

<210> SEQ ID NO 7
<211> LENGTH: 921
<212> TYPE: DNA
<213> ORGANISM: Emiliana huxleyi

<400> SEQUENCE: 7
accatgtgta aggcttctgg tcttgcttca ggtgctaaac ctgctgctgc ttcaactatt    60
gatcagtctg ctggacttgg aagagttgct gttattgttg gatctttcac tgctgctatg   120
tgttatgctc ttcaacctct tgattcacct ggtactatct atcatgattc agctgttatg   180
ggtgctcttt tgtcttggcc aatggtttac attgctcctc ttgcttacgt ttgtgctgtt   240
atggctggat gtagacttat gtcacaaaga gcttctatta agccattttt gaaacaatac   300
gttcagcctg tttacaatgt tttccaaatt gttatgtgtt cttacatggt ttggggtttg   360
gctcctaaag ttgatgttct tggacttaac cctttcgcta tgaatacaga aagagataaa   420
aagactgagt ggtttatgtt cgttcattac ctttctaaat tcgttgattg gacagatact   480
ttcttgatga ttggatctaa atcttttaga caggtttcat tcttgcaagt ttttcatcat   540
gctacagttg gtatgatttg gggtgctttg ttgagaaagg gatggggtgg aggtacttgt   600
gtttggggag ctttttattaa ctctgttaca catgttctta tgtatacaca ttacttggtt   660
acatctcttg gtcttcataa ccctcttaag tctcaactta ctaattttca acttgctcaa   720
ttcgcttcat gtgttttgca tgctgctttg gttttttgctt cagagacagt tcttcctgct   780
agacttgctt atattcaatt ggtttaccat cctactcttt tgtttctttt cggttttcag   840
atgaagtggg ttccttcttg gatcactgga caaacaatca ctggtagaga gtcagaggct   900
cctgaaaaga agttgcttg a                                              921

<210> SEQ ID NO 8
<211> LENGTH: 305
<212> TYPE: PRT
<213> ORGANISM: Emiliana huxleyi

<400> SEQUENCE: 8

Met Cys Lys Ala Ser Gly Leu Ala Ser Gly Ala Lys Pro Ala Ala
1               5                   10                  15

Ser Thr Ile Asp Gln Ser Ala Gly Leu Gly Arg Val Ala Val Ile Val
                20                  25                  30

Gly Ser Phe Thr Ala Ala Met Cys Tyr Ala Leu Gln Pro Leu Asp Ser
            35                  40                  45

Pro Gly Thr Ile Tyr His Asp Ser Ala Val Met Gly Ala Leu Leu Ser
        50                  55                  60

Trp Pro Met Val Tyr Ile Ala Pro Leu Ala Tyr Val Cys Ala Val Met
65                  70                  75                  80

Ala Gly Cys Arg Leu Met Ser Gln Arg Ala Ser Ile Lys Pro Phe Leu
                85                  90                  95

Lys Gln Tyr Val Gln Pro Val Tyr Asn Val Phe Gln Ile Val Met Cys
                100                 105                 110
```

```
Ser Tyr Met Val Trp Gly Leu Ala Pro Lys Val Asp Val Leu Gly Leu
            115                 120                 125

Asn Pro Phe Ala Met Asn Thr Glu Arg Asp Lys Lys Thr Glu Trp Phe
130                 135                 140

Met Phe Val His Tyr Leu Ser Lys Phe Val Asp Trp Thr Asp Thr Phe
145                 150                 155                 160

Leu Met Ile Gly Ser Lys Ser Phe Arg Gln Val Ser Phe Leu Gln Val
            165                 170                 175

Phe His His Ala Thr Val Gly Met Ile Trp Gly Ala Leu Leu Arg Lys
        180                 185                 190

Gly Trp Gly Gly Thr Cys Val Trp Gly Ala Phe Ile Asn Ser Val
    195                 200                 205

Thr His Val Leu Met Tyr Thr His Tyr Leu Val Thr Ser Leu Gly Leu
        210                 215                 220

His Asn Pro Leu Lys Ser Gln Leu Thr Asn Phe Gln Leu Ala Gln Phe
225                 230                 235                 240

Ala Ser Cys Val Leu His Ala Ala Leu Val Phe Ala Ser Glu Thr Val
            245                 250                 255

Leu Pro Ala Arg Leu Ala Tyr Ile Gln Leu Val Tyr His Pro Thr Leu
            260                 265                 270

Leu Phe Leu Phe Gly Phe Gln Met Lys Trp Val Pro Ser Trp Ile Thr
        275                 280                 285

Gly Gln Thr Ile Thr Gly Arg Glu Ser Glu Ala Pro Glu Lys Lys Val
        290                 295                 300

Ala
305

<210> SEQ ID NO 9
<211> LENGTH: 1368
<212> TYPE: DNA
<213> ORGANISM: Emiliana huxleyi

<400> SEQUENCE: 9
atgtcattgg ctgctaaaga tgcagcctcg gcccactcat ccgtcttgga ccctaagtat    60
cacggagcta caaataagtc aagaactgat gcagcagacc ttacagttag ttctatcgac   120
acttctaagg agatgatcat aagggggtcgt gtgtatgatg tctctgattt tattaaaagg   180
cacccgggag gaagcattat taaactctcc ttaggttctg atgcaacaga cgcttataac   240
aacttccata ttaggtctaa aaaagcggat aaaatgttga gagctttgcc aagtaggcca   300
gtagcggatg gattcgctag agacgctttg tctgcagact tcgaggccct gagagcccaa   360
ctcgaggccg aaggttactt cgaaccgaat ctgtggcatg tagcttatcg agttgcggaa   420
gtcgttgcta tgtactgggc gggtattaga cttatctggg cgggttattg gtttttagga   480
gccattgtag caggaatagc tcaggggaga tgcggttggc ttcagcatga gggtggtcat   540
tattcgctca caggtaatat taaacttgat cgacacatgc aaatgattat ctatggatta   600
ggttgcggaa tgtccggttg ttattggaga accaacata caagcacca tgcgacaccg   660
caaaagttgg gtgcagatcc agaccttcaa caatgcctc tggttgcgtt ccatggactc   720
atcggtgcta aggctagggg agcaggaaag tcgtggctag catggcaagc tccactttc   780
tttggaggcg ttatcacaac cctggtatct tttggttggc agttcgtcca acatccaaag   840
cacgcattga gagtaggaaa ccaactcgaa ttaggctata tggctttacg atatgcttta   900
tggtatgcag cattcggtca tcttgggctt ggtggtgctt tcagattgta cgcttttat   960
```

```
gtggcagtcg aggtacata tatcttcacg aactttgcgg tgtctcacac acataaggat    1020
gttgttccac acgataagca tatttcttgg accttgtatt ctgcaaacca taccactaat    1080
caatctaaca cacctctagt caattggtgg atggcctatc tgaattttca aattgaacat    1140 cacctttttcc ctagcatgcc acaatataac catcctaaaa tctgcggaag agtgaaacaa    1200
ttgtttgaaa acatggcgt agagtacgat gtcagaactt acgcgaagtc aatgcgtgat    1260
acatacgtga atctcttggc tgtgggaaat gcatctcatt cccttcatca gagaaacgag    1320
ggattaacga ctagggagtc tgcggctgtt agagttacag gtcattga    1368
```

<210> SEQ ID NO 10
<211> LENGTH: 455
<212> TYPE: PRT
<213> ORGANISM: Emiliana huxleyi

<400> SEQUENCE: 10

```
Met Ser Leu Ala Ala Lys Asp Ala Ala Ser Ala His Ser Ser Val Leu
1               5                   10                  15

Asp Pro Lys Tyr His Gly Ala Thr Asn Lys Ser Arg Thr Asp Ala Ala
            20                  25                  30

Asp Leu Thr Val Ser Ser Ile Asp Thr Ser Lys Glu Met Ile Ile Arg
        35                  40                  45

Gly Arg Val Tyr Asp Val Ser Asp Phe Ile Lys Arg His Pro Gly Gly
    50                  55                  60

Ser Ile Ile Lys Leu Ser Leu Gly Ser Asp Ala Thr Asp Ala Tyr Asn
65                  70                  75                  80

Asn Phe His Ile Arg Ser Lys Lys Ala Asp Lys Met Leu Arg Ala Leu
                85                  90                  95

Pro Ser Arg Pro Val Ala Asp Gly Phe Ala Arg Asp Ala Leu Ser Ala
            100                 105                 110

Asp Phe Glu Ala Leu Arg Ala Gln Leu Glu Ala Glu Gly Tyr Phe Glu
        115                 120                 125

Pro Asn Leu Trp His Val Ala Tyr Arg Val Ala Glu Val Val Ala Met
    130                 135                 140

Tyr Trp Ala Gly Ile Arg Leu Ile Trp Ala Gly Tyr Trp Phe Leu Gly
145                 150                 155                 160

Ala Ile Val Ala Gly Ile Ala Gln Gly Arg Cys Gly Trp Leu Gln His
                165                 170                 175

Glu Gly Gly His Tyr Ser Leu Thr Gly Asn Ile Lys Leu Asp Arg His
            180                 185                 190

Met Gln Met Ile Ile Tyr Gly Leu Gly Cys Gly Met Ser Gly Cys Tyr
        195                 200                 205

Trp Arg Asn Gln His Asn Lys His His Ala Thr Pro Gln Lys Leu Gly
    210                 215                 220

Ala Asp Pro Asp Leu Gln Thr Met Pro Leu Val Ala Phe His Gly Leu
225                 230                 235                 240

Ile Gly Ala Lys Ala Arg Gly Ala Gly Lys Ser Trp Leu Ala Trp Gln
                245                 250                 255

Ala Pro Leu Phe Phe Gly Gly Val Ile Thr Thr Leu Val Ser Phe Gly
            260                 265                 270

Trp Gln Phe Val Gln His Pro Lys His Ala Leu Arg Val Gly Asn Gln
        275                 280                 285

Leu Glu Leu Gly Tyr Met Ala Leu Arg Tyr Ala Leu Trp Tyr Ala Ala
    290                 295                 300
```

```
Phe Gly His Leu Gly Leu Gly Gly Ala Phe Arg Leu Tyr Ala Phe Tyr
305                 310                 315                 320

Val Ala Val Gly Gly Thr Tyr Ile Phe Thr Asn Phe Ala Val Ser His
            325                 330                 335

Thr His Lys Asp Val Val Pro His Asp Lys His Ile Ser Trp Thr Leu
        340                 345                 350

Tyr Ser Ala Asn His Thr Thr Asn Gln Ser Asn Thr Pro Leu Val Asn
    355                 360                 365

Trp Trp Met Ala Tyr Leu Asn Phe Gln Ile Glu His His Leu Phe Pro
370                 375                 380

Ser Met Pro Gln Tyr Asn His Pro Lys Ile Cys Gly Arg Val Lys Gln
385                 390                 395                 400

Leu Phe Glu Lys His Gly Val Glu Tyr Asp Val Arg Thr Tyr Ala Lys
                405                 410                 415

Ser Met Arg Asp Thr Tyr Val Asn Leu Leu Ala Val Gly Asn Ala Ser
            420                 425                 430

His Ser Leu His Gln Arg Asn Glu Gly Leu Thr Thr Arg Glu Ser Ala
        435                 440                 445

Ala Val Arg Val Thr Gly His
    450                 455

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ccatgggagg cgccggcgcg ag                                        22

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
ctagtccgcc ttgaggttct c                                         21

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
accatgtgca aggcgagcgg cct                                       23

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tcaccaatca tgaggaaggt                                           20
```

```
<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
ccatgggcaa gggcggcaac gc                                               22

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gggcagagat gccgcactag                                                  20

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
accatgctcg atcgcgcctc gtc                                              23

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
tcacagcgcc ttgcgggtag c                                                21

<210> SEQ ID NO 19
<211> LENGTH: 1371
<212> TYPE: DNA
<213> ORGANISM: Ostreococcus tauri

<400> SEQUENCE: 19
atgtgtgttg agaccgagaa caacgatgga atccctactg tggagatcgc tttcgatgga      60
gagagagaaa gagctgaggc taacgtgaag ttgtctgctg agaagatgga acctgctgct     120
ttggctaaga ccttcgctag aagatacgtg gttatcgagg gagttgagta cgatgtgacc     180
gatttcaaac atcctggagg aaccgtgatt ttctacgctc tctctaacac tggagctgat     240
gctactgagg ctttcaagga gttccaccac agatctagaa aggctaggaa ggcttttggct    300 gctttgcctt ctagacctgc taagaccgct aaagtggatg atgctgagat gctccaggat     360
ttcgctaagt ggagaaagga gttggagagg acggattct tcaagccttc tcctgctcat      420
gttgcttaca gattcgctga gttggctgct atgtacgctt gggaaccta cttgatgtac      480 gctagatacg ttgtgtcctc tgtgttggtt tacgcttgct tcttcggagc tagatgtgga     540
tgggttcaac atgagggagg acattcttct ttgaccggaa acatctggtg ggataagaga     600
atccaagctt tcactgctgg attcggattg ctggatctg agatatgtg gaactccatg       660 cacaacaagc accatgctac tcctcaaaaa gtgaggcacg atatggattt ggataccact     720
```

-continued

```
cctgctgttg ctttcttcaa caccgctgtg gaggataata gacctagggg attctctaag    780
tactggctca gattgcaagc ttggaccttc attcctgtga cttctggatt ggtgttgctc    840
ttctggatgt tcttcctcca tccttctaag gctttgaagg gaggaaagta cgaggagctt    900
gtgtggatgt tggctgctca tgtgattaga acctggacca ttaaggctgt tactggattc    960
accgctatgc aatcctacgg actcttcttg gctacttctt gggtttccgg atgctacttg   1020
ttcgctcact tctctacttc tcacacccat ttggatgttg ttcctgctga tgagcatttg   1080
tcttgggtta ggtacgctgt ggatcacacc attgatatcg atccttctca gggatgggtt   1140
aactggttga tgggatactt gaactgccaa gtgattcatc acctcttccc ttctatgcct   1200
caattcagac aacctgaggt gtccagaaga ttcgttgctt cgctaagaa gtggaacctc    1260 aactacaagg tgatgactta tgctggagct tggaaggcta ctttgggaaa cctcgataat   1320
gtgggaaagc actactacgt gcacggacaa cattctggaa agaccgcttg a            1371
```

<210> SEQ ID NO 20
<211> LENGTH: 456
<212> TYPE: PRT
<213> ORGANISM: Ostreococcus tauri

<400> SEQUENCE: 20

```
Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255
```

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
                340                 345                 350

Val Val Pro Ala Asp Glu His Leu Ser Trp Val Arg Tyr Ala Val Asp
            355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
                420                 425                 430

Ala Thr Leu Gly Asn Leu Asp Asn Val Gly Lys His Tyr Tyr Val His
            435                 440                 445

Gly Gln His Ser Gly Lys Thr Ala
    450                 455

<210> SEQ ID NO 21
<211> LENGTH: 873
<212> TYPE: DNA
<213> ORGANISM: Physcomitrella patens

<400> SEQUENCE: 21
atggaagttg ttgagaggtt ctacggagag ttggatggaa aggtttccca aggagtgaac      60
gctttgttgg gatctttcgg agttgagttg actgataccc aactactaa gggattgcca     120 ctcgttgatt ctccaactcc aattgtgttg gagtgtctg tttacttgac catcgtgatc     180
ggaggattgc tttggatcaa ggctagagat ctcaagccaa gagcttctga gccattcttg     240
ttgcaagctt tggtgttggt gcacaacttg ttctgcttcg ctttgtctct ttacatgtgc     300
gtgggtatcg cttaccaagc tatcacctgg agatattcct tgtggggaaa cgcttataac     360
ccaaagcaca aggagatggc tatcctcgtt tacctcttct acatgtccaa gtacgtggag     420
ttcatggata ccgtgatcat gatcctcaag agatccacca gacagatttc tttcctccac     480
gtgtaccacc attcttctat ctcccttatc tggtgggcta ttgctcatca tgctccagga     540
ggagaggctt attggagtgc tgctctcaac tctggagtgc atgtgttgat gtacgcttac     600
tacttcttgg ctgcttgctt gagatcttcc ccaaagctca agaacaagta cctcttctgg     660
ggaagatacc tcacccaatt ccagatgttc cagttcatgc tcaacttggt gcaagcttac     720
tacgatatga aaccaacgc tccatatcca caatggctca tcaagatcct cttctactac     780
atgatctccc tcttgttcct cttcggaaac ttctacgtgc aaaagtacat caagccatcc     840
gatggaaagc aaaagggagc taagaccgag tga                                   873

```
<210> SEQ ID NO 22
<211> LENGTH: 290
<212> TYPE: PRT
<213> ORGANISM: Physcomitrella patens

<400> SEQUENCE: 22

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 23
<211> LENGTH: 1197
<212> TYPE: DNA
<213> ORGANISM: Phytophtora sojae

<400> SEQUENCE: 23
atggctattt tgaaccctga ggctgattct gctgctaacc tcgctactga ttctgaggct      60
aagcaaagac aattggctga ggctggatac actcatgttg agggtgctcc tgctcctttg     120
cctttggagt tgcctcattt ctctctcaga gatctcagag ctgctattcc taagcactgc     180
ttcgagagat cttccgtgac ctccacctac tacatgatca gaacgtgtt gacttgcgct     240
```

-continued

```
gctttgttct acgctgctac cttcattgat agagctggag ctgctgctta tgttttgtgg      300
cctgtgtact ggttcttcca gggatcttac ttgactggag tgtgggttat cgctcatgag      360
tgtggacatc aggcttattg ctcttctgag gtggtgaaca acttgattgg actcgtgttg      420
cattctgctt tgttggtgcc ttaccactct tggagaatct ctcacagaaa gcaccattcc      480
aacactggat cttgcgagaa cgatgaggtt ttcgttcctg tgaccagatc tgtgttggct      540
tcttcttgga acgagacctt ggaggattct cctctctacc aactctaccg tatcgtgtac      600
atgttggttg ttggatggat gcctggatac ctcttcttca acgctactgg acctactaag      660
tactggggaa agtctaggtc tcacttcaac cctactccg ctatctatgc tgatagggag      720
agatggatga tcgtgctctc cgatattttc ttggtggcta tgttggctgt tttggctgct      780
ttggtgcaca ctttctcctt caacaccatg gtgaagttct acgtggtgcc ttacttcatt      840
gtgaacgctt acttggtgtt gattacctac ctccaacaca ccgataccta catccctcat      900
ttcagagagg gagagtggaa ttggttgaga ggagctttgt gcactgtgga tagatcattt      960
ggtccattcc tcgattctgt ggtgcataga atcgtggata cccatgtttg ccaccacatc     1020
ttctccaaga tgccttttcta tcattgcgag gaggctacca acgctattaa gcctctcctc     1080
ggaaagttct acttgaagga taccactcct gttcctgttg ctctctggag atcttacacc     1140
cattgcaagt tcgttgagga tgatggaaag gtggtgttct acaagaacaa gctctag       1197
```

<210> SEQ ID NO 24
<211> LENGTH: 398
<212> TYPE: PRT
<213> ORGANISM: Phytophtora sojae

<400> SEQUENCE: 24

Met Ala Ile Leu Asn Pro Glu Ala Asp Ser Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
210                 215                 220
Ser Arg Ser His Phe Asn Pro Tyr Ser Ala Ile Tyr Ala Asp Arg Glu
225                 230                 235                 240
Arg Trp Met Ile Val Leu Ser Asp Ile Phe Leu Val Ala Met Leu Ala
                245                 250                 255
Val Leu Ala Ala Leu Val His Thr Phe Ser Phe Asn Thr Met Val Lys
            260                 265                 270
Phe Tyr Val Val Pro Tyr Phe Ile Val Asn Ala Tyr Leu Val Leu Ile
        275                 280                 285
Thr Tyr Leu Gln His Thr Asp Thr Tyr Ile Pro His Phe Arg Glu Gly
    290                 295                 300
Glu Trp Asn Trp Leu Arg Gly Ala Leu Cys Thr Val Asp Arg Ser Phe
305                 310                 315                 320
Gly Pro Phe Leu Asp Ser Val Val His Arg Ile Val Asp Thr His Val
                325                 330                 335
Cys His His Ile Phe Ser Lys Met Pro Phe Tyr His Cys Glu Glu Ala
            340                 345                 350
Thr Asn Ala Ile Lys Pro Leu Leu Gly Lys Phe Tyr Leu Lys Asp Thr
        355                 360                 365
Thr Pro Val Pro Val Ala Leu Trp Arg Ser Tyr Thr His Cys Lys Phe
    370                 375                 380
Val Glu Asp Asp Gly Lys Val Val Phe Tyr Lys Asn Lys Leu
385                 390                 395

<210> SEQ ID NO 25
<211> LENGTH: 819
<212> TYPE: DNA
<213> ORGANISM: Thalassiosira pseudonana

<400> SEQUENCE: 25
atggatgctt ataacgctgc tatggataag attggagctg ctatcatcga ttggagtgat      60
ccagatggaa agttcagagc tgatagggag gattggtggt tgtgcgattt cagatccgct     120
atcaccattg ctctcatcta catcgctttc gtgatcttgg atctgctgt gatgcaatct      180 ctcccagcta tggaccccata ccctatcaag ttcctctaca acgtgtctca aatcttcctc     240
tgcgcttaca tgactgttga ggctggattc ctcgcttata ggaacggata caccgttatg     300
ccatgcaacc acttcaacgt gaacgatcca ccagttgcta cttgctctg gctcttctac      360 atctccaaag tgtgggattt ctgggatacc atcttcattg tgctcggaaa gaagtggaga     420
caactctctt tcttgcacgt gtaccatcat accaccatct tcctcttcta ctggttgaac    480
gctaacgtgc tctacgatgg agatatcttc ttgaccatcc tcctcaacgg attcattcac    540
accgtgatgt acacctacta cttcatctgc atgcacacca aggattctaa gaccggaaag    600
tctttgccaa tctggtggaa gtcatctttg accgctttcc aactcttgca attcaccatc    660
atgatgtccc aagctaccta cttggttttc cacggatgcg ataaggtttc cctcagaatc    720
accatcgtgt acttcgtgta cattctctcc ctttcttcc tcttcgctca gttcttcgtg    780
caatcctaca tggctccaaa gaagaagaag tccgcttga                            819

<210> SEQ ID NO 26
<211> LENGTH: 272
<212> TYPE: PRT
<213> ORGANISM: Thalassiosira pseudonana

<400> SEQUENCE: 26

```
Met Asp Ala Tyr Asn Ala Ala Met Asp Lys Ile Gly Ala Ala Ile Ile
1               5                   10                  15
Asp Trp Ser Asp Pro Asp Gly Lys Phe Arg Ala Asp Arg Glu Asp Trp
            20                  25                  30
Trp Leu Cys Asp Phe Arg Ser Ala Ile Thr Ile Ala Leu Ile Tyr Ile
        35                  40                  45
Ala Phe Val Ile Leu Gly Ser Ala Val Met Gln Ser Leu Pro Ala Met
    50                  55                  60
Asp Pro Tyr Pro Ile Lys Phe Leu Tyr Asn Val Ser Gln Ile Phe Leu
65                  70                  75                  80
Cys Ala Tyr Met Thr Val Glu Ala Gly Phe Leu Ala Tyr Arg Asn Gly
                85                  90                  95
Tyr Thr Val Met Pro Cys Asn His Phe Asn Val Asn Asp Pro Pro Val
            100                 105                 110
Ala Asn Leu Leu Trp Leu Phe Tyr Ile Ser Lys Val Trp Asp Phe Trp
        115                 120                 125
Asp Thr Ile Phe Ile Val Leu Gly Lys Lys Trp Arg Gln Leu Ser Phe
    130                 135                 140
Leu His Val Tyr His His Thr Thr Ile Phe Leu Phe Tyr Trp Leu Asn
145                 150                 155                 160
Ala Asn Val Leu Tyr Asp Gly Asp Ile Phe Leu Thr Ile Leu Leu Asn
                165                 170                 175
Gly Phe Ile His Thr Val Met Tyr Thr Tyr Tyr Phe Ile Cys Met His
            180                 185                 190
Thr Lys Asp Ser Lys Thr Gly Lys Ser Leu Pro Ile Trp Trp Lys Ser
        195                 200                 205
Ser Leu Thr Ala Phe Gln Leu Leu Gln Phe Thr Ile Met Met Ser Gln
    210                 215                 220
Ala Thr Tyr Leu Val Phe His Gly Cys Asp Lys Val Ser Leu Arg Ile
225                 230                 235                 240
Thr Ile Val Tyr Phe Val Tyr Ile Leu Ser Leu Phe Phe Leu Phe Ala
                245                 250                 255
Gln Phe Phe Val Gln Ser Tyr Met Ala Pro Lys Lys Lys Ser Ala
            260                 265                 270
```

<210> SEQ ID NO 27
<211> LENGTH: 1086
<212> TYPE: DNA
<213> ORGANISM: Phytophtora infestans

<400> SEQUENCE: 27

```
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg     120
atcgcggtgg ctctaacctt cggtctcaac tacgctcgcg ctctgcccga ggtcgagagc     180
ttctgggctc tggacgccgc actctgcacg gctacatct tgctgcaggg catcgtgttc      240
tggggcttct tcacggtggg ccacgatgcc ggccacggcg ccttctcgcg ctaccacctg     300
cttaacttcg tggtgggcac tttcatgcac tcgctcatcc tcacgccctt cgagtcgtgg     360
aagctcacgc accgtcacca ccacaagaac acgggcaaca ttgaccgtga cgaggtcttc     420
tacccgcaac gcaaggccga cgaccaccg ctgtctcgca acctgattct ggcgctcggg      480
gcagcgtggc tcgcctattt ggtcgagggc ttccctcctc gtaaggtcaa ccacttcaac     540
```
ccgttcgagc ctctgttcgt gcgtcaggtg tcagctgtgg taatctctct tctcgcccac 600
ttcttcgtgg ccggactctc catctatctg agcctccagc tgggccttaa gacgatggca 660
atctactact atggacctgt ttttgtgttc ggcagcatgc tggtcattac caccttccta 720
caccacaatg atgaggagac cccatggtac gccgactcgg agtggacgta cgtcaagggc 780
aacctctcgt ccgtggaccg atcgtacggc gcgctcattg acaacctgag ccacaacatc 840
ggcacgcacc agatccacca ccttttccct atcattccgc actacaaact caagaaagcc 900
actgcggcct tccaccaggc tttccctgag ctcgtgcgca agagcgacga gccaattatc 960
aaggctttct tccgggttgg acgtctctac gcaaactacg gcgttgtgga ccaggaggcg 1020
aagctcttca cgctaaagga agccaaggcg gcgaccgagg cggcggccaa gaccaagtcc 1080
acgtaa 1086

<210> SEQ ID NO 28
<211> LENGTH: 361
<212> TYPE: PRT
<213> ORGANISM: Phytophtora infestans

<400> SEQUENCE: 28

Met Ala Thr Lys Glu Ala Tyr Val Phe Pro Thr Leu Thr Glu Ile Lys
1 5 10 15

Arg Ser Leu Pro Lys Asp Cys Phe Glu Ala Ser Val Pro Leu Ser Leu
20 25 30

Tyr Tyr Thr Val Arg Cys Leu Val Ile Ala Val Ala Leu Thr Phe Gly
35 40 45

Leu Asn Tyr Ala Arg Ala Leu Pro Glu Val Glu Ser Phe Trp Ala Leu
50 55 60

Asp Ala Ala Leu Cys Thr Gly Tyr Ile Leu Leu Gln Gly Ile Val Phe
65 70 75 80

Trp Gly Phe Phe Thr Val Gly His Asp Ala Gly His Gly Ala Phe Ser
85 90 95

Arg Tyr His Leu Leu Asn Phe Val Val Gly Thr Phe Met His Ser Leu
100 105 110

Ile Leu Thr Pro Phe Glu Ser Trp Lys Leu Thr His Arg His His His
115 120 125

Lys Asn Thr Gly Asn Ile Asp Arg Asp Glu Val Phe Tyr Pro Gln Arg
130 135 140

Lys Ala Asp Asp His Pro Leu Ser Arg Asn Leu Ile Leu Ala Leu Gly
145 150 155 160

Ala Ala Trp Leu Ala Tyr Leu Val Glu Gly Phe Pro Pro Arg Lys Val
165 170 175

Asn His Phe Asn Pro Phe Glu Pro Leu Phe Val Arg Gln Val Ser Ala
180 185 190

Val Val Ile Ser Leu Leu Ala His Phe Phe Val Ala Gly Leu Ser Ile
195 200 205

Tyr Leu Ser Leu Gln Leu Gly Leu Lys Thr Met Ala Ile Tyr Tyr Tyr
210 215 220

Gly Pro Val Phe Val Phe Gly Ser Met Leu Val Ile Thr Thr Phe Leu
225 230 235 240

His His Asn Asp Glu Glu Thr Pro Trp Tyr Ala Asp Ser Glu Trp Thr
245 250 255

Tyr Val Lys Gly Asn Leu Ser Ser Val Asp Arg Ser Tyr Gly Ala Leu
260 265 270

```
Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360

<210> SEQ ID NO 29
<211> LENGTH: 1434
<212> TYPE: DNA
<213> ORGANISM: Claviceps purpurea

<400> SEQUENCE: 29
atggctgcta ctacctctgc tatgagcaag gatgctgttc ttagaagaac tgctgctgct      60
actactgcta tcgatcacga aagctctacc tctgcttctc cagctgattc tcctagactc     120
tctgcttctt ctacctctct ctcttctctc agctctctcg acgctaagga taaggatgat     180
gagtacgctg gacttcttga tacttacgga aacgctttca cccctcctga tttcactatc     240
aaggatatca gagatgctat ccctaagcac tgcttcgagc gttctgctat caagggatac     300
gcttatatcc tcagagatgt ggcttgcctt tctaccactt tctacctctt ccacaacttc     360
gttacccctg agaacgttcc ttacacccct cttagagttt tcctctgggg agtttacact     420
gctcttcagg gacttttcgg aactggactc tggattatcg ctcacgagtg tggacacggt     480
gctttctctc cttctaccct cactaacgat cttactggat gggttctcca ctctgctctt     540
ctcgtgcctt acttctcttg gaagttctct cactctgctc accacaaggg aaccggaaat     600
atggaaaggg atatggcttt cctccctaga actagggctc aatacgctac cagattcgga     660
agagctatgg atcagcttgg agatctttgc gaggaaaccc ctatctacac tgctggattc     720
cttgttttcc agcagcttct tggatggcct tcttacttga tcgctaacgt tactggacac     780
gatcttcacg agagacagag agagggaaga ggaaagggaa agaagaacgg attcggagga     840
actgttaacc acttcgaccc tcgttctcct atcttcgatg acaagcacgc taagtttatc     900
gttctcagcg atatcggact tggacttgct atcgctgctc ttgtttacct cggaaacaga     960
ttcggatggg ctaacgttgc tgtttggtac ttcgttcctt acctctgggt taaccactgg    1020
atcgttgcta tcactttcct tcagcacact gatcctactc ttcctcacta cactgctgag    1080
gaatggaact tcgttcgtgg agctgctgct acaatcgata gagagatggg atttatcggt    1140
agacacctct tccacggaat cgttgagact cacgtgcttc accactacgt ttcttcaatc    1200
cctttctaca acgctgatga ggcttctgag gctatcaagc ctgttatggg aaagcactac    1260
cgttctgaga ctaaggatgg acctatgggt tttatcaggg ctttgtggaa aactgctaga    1320
tggtgtcaat gggttgagcc ttctgctgat gctcaaggtg ctggtgaagg tgttctcttc    1380
ttcaggaaca gaaacggact tggaactaag cctatctcta tgaggaccca gtga          1434

<210> SEQ ID NO 30
<211> LENGTH: 477
<212> TYPE: PRT
<213> ORGANISM: Claviceps purpurea
```

```
<400> SEQUENCE: 30

Met Ala Ala Thr Thr Ser Ala Met Ser Lys Asp Ala Val Leu Arg Arg
1               5                   10                  15

Thr Ala Ala Thr Thr Ala Ile Asp His Glu Ser Ser Thr Ser Ala
            20                  25                  30

Ser Pro Ala Asp Ser Pro Arg Leu Ser Ala Ser Ser Thr Ser Leu Ser
            35                  40                  45

Ser Leu Ser Ser Leu Asp Ala Lys Asp Lys Asp Glu Tyr Ala Gly
    50                  55                  60

Leu Leu Asp Thr Tyr Gly Asn Ala Phe Thr Pro Pro Asp Phe Thr Ile
65                  70                  75                  80

Lys Asp Ile Arg Asp Ala Ile Pro Lys His Cys Phe Glu Arg Ser Ala
                85                  90                  95

Ile Lys Gly Tyr Ala Tyr Ile Leu Arg Asp Val Ala Cys Leu Ser Thr
                100                 105                 110

Thr Phe Tyr Leu Phe His Asn Phe Val Thr Pro Glu Asn Val Pro Tyr
            115                 120                 125

Thr Pro Leu Arg Val Phe Leu Trp Gly Val Tyr Thr Ala Leu Gln Gly
            130                 135                 140

Leu Phe Gly Thr Gly Leu Trp Ile Ile Ala His Glu Cys Gly His Gly
145                 150                 155                 160

Ala Phe Ser Pro Ser Thr Leu Thr Asn Asp Leu Thr Gly Trp Val Leu
                165                 170                 175

His Ser Ala Leu Leu Val Pro Tyr Phe Ser Trp Lys Phe Ser His Ser
            180                 185                 190

Ala His His Lys Gly Thr Gly Asn Met Glu Arg Asp Met Ala Phe Leu
            195                 200                 205

Pro Arg Thr Arg Ala Gln Tyr Ala Thr Arg Phe Gly Arg Ala Met Asp
210                 215                 220

Gln Leu Gly Asp Leu Cys Glu Glu Thr Pro Ile Tyr Thr Ala Gly Phe
225                 230                 235                 240

Leu Val Phe Gln Gln Leu Leu Gly Trp Pro Ser Tyr Leu Ile Ala Asn
                245                 250                 255

Val Thr Gly His Asp Leu His Glu Arg Gln Arg Glu Gly Arg Gly Lys
            260                 265                 270

Gly Lys Lys Asn Gly Phe Gly Gly Thr Val Asn His Phe Asp Pro Arg
            275                 280                 285

Ser Pro Ile Phe Asp Asp Lys His Ala Lys Phe Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Val Ala Val Trp Tyr Phe Val Pro Tyr Leu Trp
                325                 330                 335

Val Asn His Trp Ile Val Ala Ile Thr Phe Leu Gln His Thr Asp Pro
            340                 345                 350

Thr Leu Pro His Tyr Thr Ala Glu Glu Trp Asn Phe Val Arg Gly Ala
            355                 360                 365

Ala Ala Thr Ile Asp Arg Glu Met Gly Phe Ile Gly Arg His Leu Phe
370                 375                 380

His Gly Ile Val Glu Thr His Val Leu His His Tyr Val Ser Ser Ile
385                 390                 395                 400

Pro Phe Tyr Asn Ala Asp Glu Ala Ser Glu Ala Ile Lys Pro Val Met
            405                 410                 415
```

```
Gly Lys His Tyr Arg Ser Glu Thr Lys Asp Gly Pro Met Gly Phe Ile
            420                 425                 430

Arg Ala Leu Trp Lys Thr Ala Arg Trp Cys Gln Trp Val Glu Pro Ser
        435                 440                 445

Ala Asp Ala Gln Gly Ala Gly Glu Gly Val Leu Phe Phe Arg Asn Arg
    450                 455                 460

Asn Gly Leu Gly Thr Lys Pro Ile Ser Met Arg Thr Gln
465                 470                 475

<210> SEQ ID NO 31
<211> LENGTH: 903
<212> TYPE: DNA
<213> ORGANISM: Ostreococcus tauri

<400> SEQUENCE: 31
atgtctgctt ctggagcttt gttgcctgct attgctttcg ctgcttacgc ttacgctacc      60
tacgcttatg ctttcgagtg gtctcatgct aacggaatcg ataacgtgga tgctagagag     120
tggattgagg ctttgtcttt gagactccct gcaattgcta ccaccatgta cctcttgttc     180
tgccttgtgg gacctagatt gatggctaag agggaggctt ttgatcctaa gggattcatg     240
ctcgcttaca acgcttacca aaccgctttc aacgttgtgg tgctcggaat gttcgctaga     300
gagatctctg gattgggaca acctgtttgg ggatctacta tgccttggag cgataggaag     360
tccttcaaga ttttgttggg agtgtggctc cattacaaca ataagtacct cgagttgttg     420
gatactgtgt tcatggtggc taggaaaaag accaagcagc tctcttttct tgcatgtgta c     480 catcatgctt tgttgatttg gcttggtgg cttgtttgtc atctcatggc taccaacgat      540
tgcatcgatg cttatttcgg agctgcttgc aactcttttca tccacatcgt gatgtactcc     600
tactacctca tgtctgcttt gggaattaga tgcccttgga agagatatat cacccaggct     660
cagatgttgc aattcgtgat cgtgttcgct catgctgttt tcgtgctcag acaaaagcac     720
tgccctgtta ctttgccttg ggcacaaatg ttcgtgatga caaatatgtt ggtgctcttc     780
ggaaacttct acctcaaggc ttactctaac aagtctaggg gagatggagc ttcttctgtt     840
aagcctgctg agactactag agcaccttct gtgagaagaa ccaggtccag gaagatcgat     900
tga                                                                   903

<210> SEQ ID NO 32
<211> LENGTH: 300
<212> TYPE: PRT
<213> ORGANISM: Ostreococcus tauri

<400> SEQUENCE: 32

Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Val Leu Gly
                85                  90                  95
```

-continued

```
Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
            115                 120                 125

Trp Leu His Tyr Asn Asn Lys Tyr Leu Glu Leu Leu Asp Thr Val Phe
            130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
            165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
            195                 200                 205

Ile Arg Cys Pro Trp Lys Arg Tyr Ile Thr Gln Ala Gln Met Leu Gln
            210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
290                 295                 300
```